(12) United States Patent
Sankai

(10) Patent No.: US 9,539,162 B2
(45) Date of Patent: Jan. 10, 2017

(54) WEARING TYPE BEHAVIOR HELP DEVICE, WEARING TYPE BEHAVIOR HELP DEVICE CALIBRATION DEVICE, AND CALIBRATION PROGRAM

(75) Inventor: Yoshiyuki Sankai, Tsukuba (JP)

(73) Assignee: UNIVERSITY OF TSUKUBA, Ibaraki (JP)

( * ) Notice: Subject to any disclaimer, the term of this patent is extended or adjusted under 35 U.S.C. 154(b) by 1453 days.

(21) Appl. No.: 10/592,303

(22) PCT Filed: Feb. 2, 2005

(86) PCT No.: PCT/JP2005/001516
§ 371 (c)(1),
(2), (4) Date: Sep. 11, 2006

(87) PCT Pub. No.: WO2005/087172
PCT Pub. Date: Sep. 22, 2005

(65) Prior Publication Data
US 2008/0234608 A1    Sep. 25, 2008

(30) Foreign Application Priority Data

Mar. 11, 2004    (JP) .................................. 2004-068790

(51) Int. Cl.
*A61H 3/00* (2006.01)
*A61H 1/02* (2006.01)
(Continued)

(52) U.S. Cl.
CPC .............. *A61H 3/00* (2013.01); *A61B 5/04888* (2013.01); *A61B 5/4528* (2013.01);
(Continued)

(58) Field of Classification Search
CPC ................. A61H 3/00; A61H 2003/001; A61H 2003/002;A61H 2003/007; A61H 2001/0211; A61H 1/0262; A61H 1/0237; A61H 2201/50; A61H 2201/5007; B25J 9/0006
(Continued)

(56) References Cited

U.S. PATENT DOCUMENTS 3,923,045 A * 12/1975 Talati et al. ...................... 601/34
3,993,056 A * 11/1976 Rabischong et al. ........... 602/13
(Continued)

FOREIGN PATENT DOCUMENTS

| EP | 1 324 403 | 7/2003 |
|---|---|---|
| EP | 1 661 543 | 5/2006 |

(Continued)

OTHER PUBLICATIONS

Kawamoto et al., "Power Assist System HAL-3 for Gait Disorder Person", 2002, Springer-Verlag Berlin Heidelberg, ICCHP, pp. 196-203.*

(Continued)

*Primary Examiner* — Justine Yu
*Assistant Examiner* — Colin W Stuart
(74) *Attorney, Agent, or Firm* — Ladas & Parry LLP

(57) ABSTRACT

[Problem to be Solved]
The problem to be solved by the present invention is to reduce the load applied to the wearer by correcting a parameter in correspondence with detectivity of biosignals.
[Means to Solve Problem]
The calibration controlling part 162 of the movement assisting apparatus 10 enables the power amplifying part 158 to apply a driving force of the driving source 140 as a load (input torque) from the load generating part 164 to the wearer 12 when the wearer 12 wears the movement assisting wearing device. Then, the wearer 12 applied with the driving force of the driving source 140 generates power from the (Continued)

skeletal muscles by performing a predetermined calibration operation. Accordingly, the physical phenomenon detecting part 142 detects joint angle along with the calibration operation, and the biosignal detecting part 144 detects myoelectric signals. In the parameter correction part 156, a parameter K is corrected based on the difference between the load (input torque) and the driving force (muscular strength) being calculated by the difference deriving part 154 with respect to the phase identified by the phase identifying part 152.

11 Claims, 22 Drawing Sheets

(51) Int. Cl.
    *A61B 5/0488*      (2006.01)
    *A61B 5/00*      (2006.01)
    *B25J 9/00*      (2006.01)
    *A61B 5/107*      (2006.01)

(52) U.S. Cl.
    CPC .......... *A61H 1/0237* (2013.01); *A61H 1/0262* (2013.01); *B25J 9/0006* (2013.01); *A61B 5/1071* (2013.01); *A61H 2003/007* (2013.01)

(58) Field of Classification Search
    USPC ... 601/5, 23, 27, 29, 32, 33, 34, 35; 607/48, 607/49
    See application file for complete search history.

(56) References Cited

U.S. PATENT DOCUMENTS

| | | | | |
|---|---|---|---|---|
| 5,282,460 | A * | 2/1994 | Boldt | 601/5 |
| 6,213,922 | B1 * | 4/2001 | Afanasenko et al. | 482/124 |
| 6,872,187 | B1 * | 3/2005 | Stark et al. | 602/16 |
| 7,066,896 | B1 * | 6/2006 | Kiselik | 601/5 |
| 2006/0211956 | A1 * | 9/2006 | Sankai | 601/5 |
| 2008/0161937 | A1 * | 7/2008 | Sankai | 623/25 |

FOREIGN PATENT DOCUMENTS

| | | |
|---|---|---|
| JP | 61-34340 | 8/1986 |
| JP | 7-163607 | 6/1995 |
| JP | 2002-301124 | 10/2002 |
| JP | 2002301124 A * | 10/2002 |
| JP | 2003-79684 | 3/2003 |
| WO | 01/13778 | 3/2001 |
| WO | 03/032833 | 4/2003 |

OTHER PUBLICATIONS

Patent Abstracts of Japan of 2003-79684 dated Mar. 18, 2003.
Patent Abstracts of Japan of 2002-301124 dated Oct. 15, 2002.
Patent Abstracts of Japan of 7-163607 dated Jun. 27, 1995.
Erfanian, A., et al. "Using Evoked EMG as a Synthetic Force Sensor of Isometric Electrically Stimulated Muscle." IEEE Transactions on Biomedical Engineering (1998) vol. 45, No. 2 pp. 188-202.
Nakai, T., et al. "Study of Power Assistive Leg for Walking Aid Using EMG" (2001).
Lee, S., et al. "Power Assist Control for Leg with HAL-3"
Kawamura, Y., et al. "Study on Exoskeleton Power Assist HAL for Walking Aid Using EMG" (2000).
Sankai, Y., et al. "Study of Hybrid Power Assist System HAL-1 for Walking Aid using EMG" (2000).
Japanese Office Action Issued in Application No. 2010-181601 on Jul. 3, 2012 (With Translation).
Imai, et al., The Development of Motion Acquiring and Learning System to Realize Human-Like Motion (Pertinent Portion).
Partial English translation of Japanese Publication No. JP61-34340.

* cited by examiner

FIG.8

| TASK A (LOAD 1) | PHASE A1 | MUSCULAR STRENGTH | EMGknee | PARAMETER | |
|---|---|---|---|---|---|
| | PHASE A1 | eA1(t) | EA1(t) | KA1 | ⋮ |
| | PHASE A2 | eA2(t) | EA2(t) | KA2 | ⋮ |
| | PHASE A3 | eA3(t) | EA3(t) | KA3 | ⋮ |
| | PHASE A4 | eA4(t) | EA4(t) | KA4 | ⋮ |
| TASK B (LOAD 2) | PHASE B1 | ⋮ | ⋮ | ⋮ | ⋮ |
| | PHASE B2 | ⋮ | ⋮ | ⋮ | ⋮ |
| | PHASE B3 | ⋮ | ⋮ | ⋮ | ⋮ |
| | PHASE B4 | ⋯ | ⋯ | ⋯ | ⋯ |
| ⋯ | ⋯ | | | | |

CALIBRATION DATABASE ~148

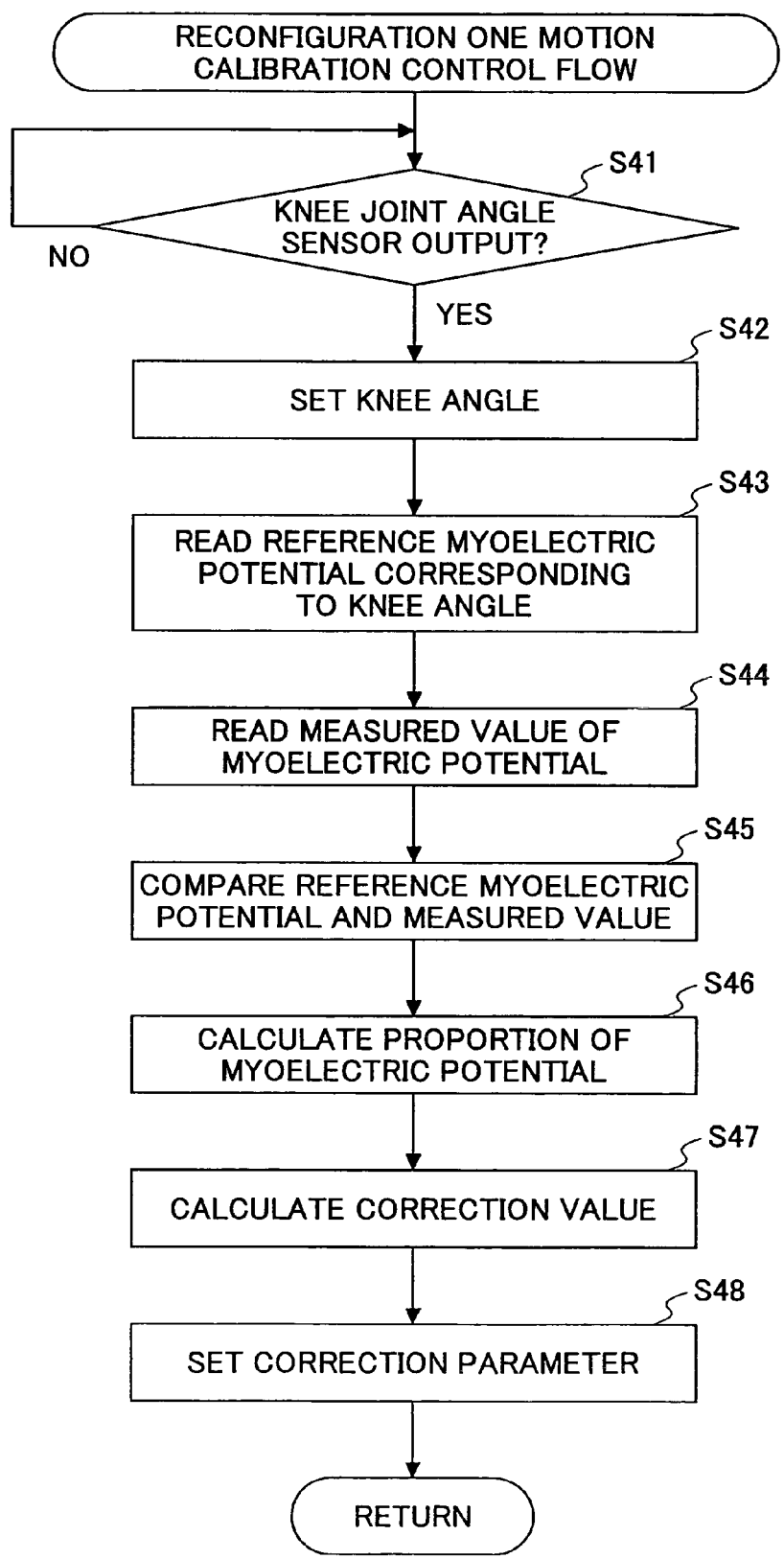

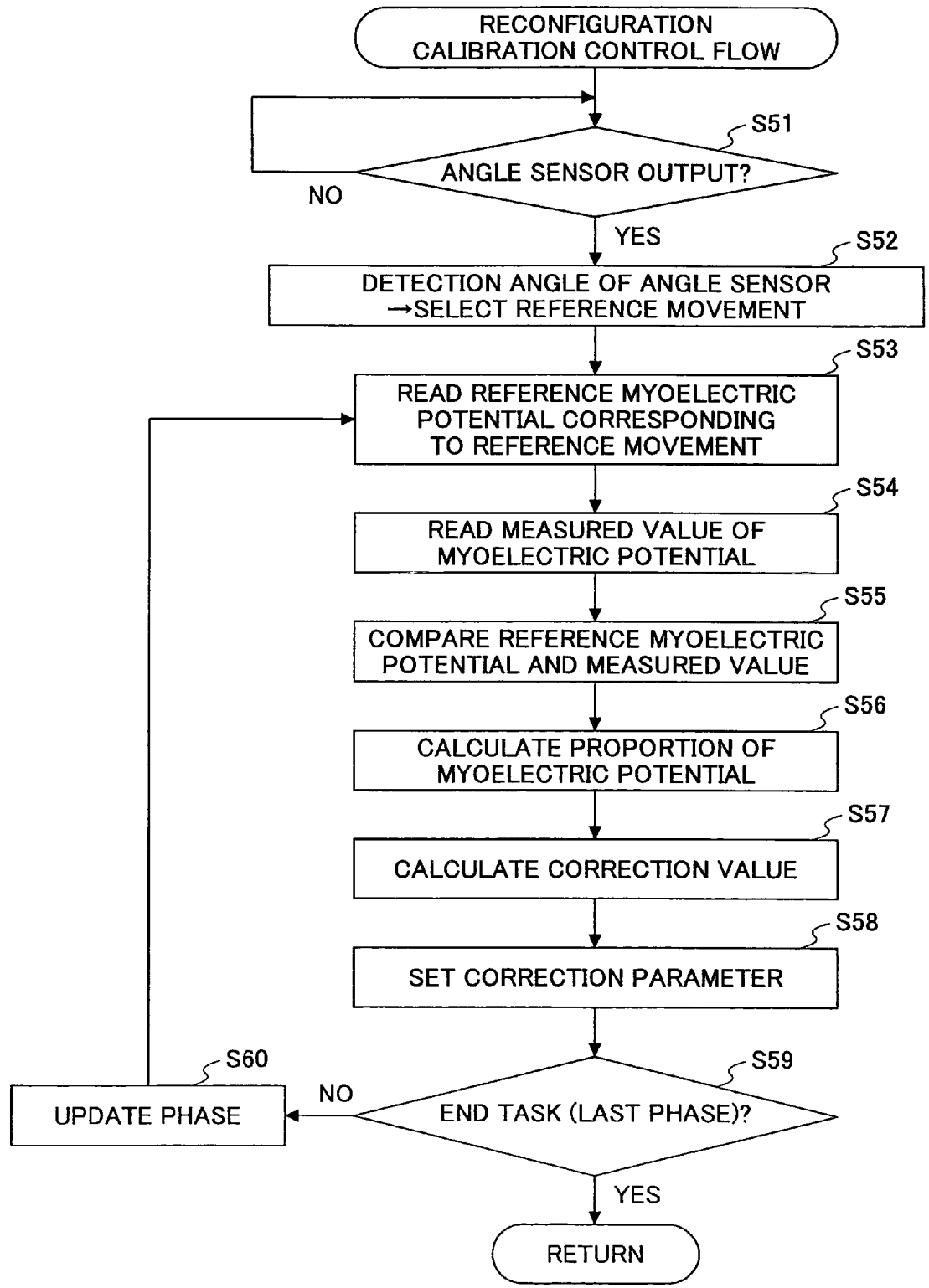

WEARING TYPE BEHAVIOR HELP DEVICE, WEARING TYPE BEHAVIOR HELP DEVICE CALIBRATION DEVICE, AND CALIBRATION PROGRAM

TECHNICAL FIELD

The present invention relates to a wearable type movement assisting apparatus, and more particularly to a wearable type movement assisting apparatus for assisting or substituting for the movement of the wearer, a calibration apparatus of a wearable type movement assisting apparatus, a calibration method for a wearable type movement assisting apparatus, and modification of a calibration program.

BACKGROUND ART

Movements which can be easily performed by an able-bodied person are often extremely difficult to perform for a physically disabled person having lost his/her muscular strength or an elderly person having deteriorated muscular strength. Therefore, development of various power assisting apparatuses are being promoted these days for assisting or substituting for movement of such people.

One of such power assisting apparatuses is, for example, a wearable type movement assisting apparatus (hereinafter simply referred to as "movement assisting apparatus") that is worn by the user (hereinafter referred to as "wearer").

Such types of movement assisting apparatuses include one that is developed with a configuration including a myoelectric potential sensor (detecting part) for detecting a myoelectric potential signal (biosignal) associated with muscular activity of the wearer and an actuator for applying assisting power to the wearer (for example, non-patent document 1).

This movement assisting apparatus has a characteristic of driving the actuator (e.g. motor) based on detection results from the detecting part and controlling the actuator by a computer for applying assisting force (assisting power) according to the will of the wearer. Accordingly, the movement assisting apparatus can apply assisting force to the wearer based on the will of the wearer and provide an assisting force required for the movement of the wearer in cooperation with the movement of the wearer.

Meanwhile, the above-described movement assisting apparatus generates an assisting force for satisfying a necessary correlation with respect to myoelectric potential signals emitted from the wearer, for example, by supplying control signals having a predetermined correlation with respect to amplified detection signals of a myoelectric potential sensor to a driver circuit that controls the actuator.

That is, since myoelectric signals and movement corresponding to muscular activity of the wearer have a positive correlation and their proportion becomes a certain value, it is necessary to apply an assisting force corresponding to myoelectric signals so as to satisfy such relationships. In other words, unless the assisting force of the movement assisting apparatus satisfies a certain relationship with respect to myoelectric potential signals, the assisting power applied to the wearer may become too much or too little, and may adversely affect the user.

The myoelectric potential signals emitted by the wearer are weak electric signals. Furthermore, the proportional relationship between myoelectric potential signals and muscular strength corresponding to the myoelectric potential signals differs depending on each individual. Moreover, the electric resistance value of skin is not constant even for the same person depending on his/her daily condition. Accordingly, there are many cases where the myoelectric potential signals and the muscular strength generated according to the myoelectric potential signals are not constant. Therefore, the movement assisting apparatus is installed with a so-called calibration apparatus for correcting a controlled variable with respect to an actuator by multiplying the variable by a predetermined coefficient (parameter) to obtain a control signal. More specifically, a calibration apparatus is provided for associating myoelectric potential signals and assisting force with a certain relationship and performing correction by using a coefficient (parameter) in a case where the movement assisting apparatus is worn by the wearer. This calibration apparatus is configured to correct a controlled variable by obtaining myoelectric potential signals generated when a certain amount of load is applied to the wearer and deriving and changing the above-described coefficient (parameter) in accordance with the corresponding relationship between the load and the myoelectric potential signals.

In a case where the calibration apparatus changes the load applied to the wearer step by step and provides muscular strength to the wearer for counterbalancing the load in each step, the calibration apparatus can associate myoelectric signals and assisting power to establish a certain relationship based on the corresponding relationships between the load and the myoelectric potential signals of each step.

As a method of changing the load applied to the wearer step by step, there is a method of preparing poises of various weights and exchanging the poises whenever a surface myoelectric signal is detected, or a method of connecting a coil spring to the leg of the wearer and changing the amount of expansion of the coil spring step by step.

With the movement assisting apparatus including a calibration apparatus using these methods, myoelectric potential signals and assisting power can be reliably associated by a certain relationship according to necessity. Accordingly, the assisting force applied to the wearer can be prevented from becoming too much or too little.

Non-Patent Document 1: Takao Nakai, Suwoong Lee, Hiroaki Kawamoto and Yoshiyuki Sankai, "Development of Power Assistive Leg for Walking Aid using EMG and Linux," Second Asian Symposium on Industrial Automation and Robotics, BITECH, Bangkok, Thailand, May 17-18, 2001

DISCLOSURE OF INVENTION

Problem to be Solved by the Invention

Meanwhile, as described above, the above-described movement assisting apparatus is configured to have a myoelectric potential sensor directly adhered to the skin of the wearer and detect surface myoelectric potential through the skin. Since the value of electric resistance may differ or change even with the same person due to, for example, deviation in the adhered position of the myoelectric potential sensor or changes of physical conditions, it is necessary to perform the above-described correction (calibration) each time the movement assisting apparatus is worn. Therefore, the wearer is forced to perform complicated procedures whenever the movement assisting apparatus is worn by the wearer, for example, in a case of the above-described calibration methods, exchanging poises of different weights or attaching a coil spring and changing the amount of expansion of the coil spring step by step.

With the conventional calibration methods, the procedures required for an individual wearer to perform calibration become complicated. This not only requires a considerable amount of time for finishing the calibration, but also places an unnecessary burden on a weak-muscled wearer. These reasons serve as an obstacle to putting the movement assisting apparatus into practical use and popularizing the movement assisting apparatus.

Therefore, taking the above-described situation into consideration, the present invention is aimed at solving the above-described problems by correcting parameters that would reduce the burden of the wearer when performing calibration.

Means for Solving Problem

In order to solve the above-described problems, the present invention includes the following.

In claim 1 of the present invention, there is provided a wearable type movement assisting apparatus including a detecting part for detecting a biosignal from a wearer, a movement assisting wearing device including a driving source for applying a driving force to the wearer, and a control part for controlling the driving source to generate an assisting force according to a detection signal detected by the detecting part, the wearable type movement assisting apparatus characterized by comprising: a calibration part for detecting the biosignal corresponding to the driving force applied as a load from the driving source and setting a correction value based on the detected signal.

In claim 2 of the present invention, there is provided a wearable type movement assisting apparatus including a detecting part for detecting a biosignal from a wearer, a movement assisting wearing device including a driving source for applying a driving force to the wearer, and a control part for controlling the driving source to generate an assisting force according to a detection signal detected by the detecting part, the wearable type movement assisting apparatus characterized by comprising: a load generating part for applying a predetermined driving force from the driving source as an external force when the movement assisting wearing device is worn by the wearer; and a correction value setting part for generating a parameter for a calculation process executed in accordance with the detection signal by the control part and setting the parameter as a correction value for the wearer.

In claim 3 of the present invention, there is provided the wearable type movement assisting apparatus characterized in that the calibration part includes a database storing a corresponding relationship between the detection signal detected by the detecting part and a control signal for controlling the driving source, wherein the control part corrects the control signal stored in the database according to the correction value set by the correction value setting part.

In claim 4 of the present invention, there is provided the wearable type movement assisting apparatus characterized in that the detecting part is adhered on the skin of the wearer and detects a myoelectric potential of the wearer as the biosignal.

In claim 5 of the present invention, there is provided the wearable type movement assisting apparatus characterized in that the movement assisting wearing device includes a waist belt, a right leg assisting part provided at the right side below the waist belt, and a left leg assisting part provided at the left side below the waist belt, wherein the right leg assisting part and the left leg assisting part includes a first frame extending downward in a manner supporting the waist belt, a second frame extending downward from the first frame, a third frame extending downward from the second frame, a fourth frame on which a bottom side of the foot of the wearer is placed and provided at a lower end of the third frame, a first joint interposed between a lower end of the first frame and an upper end of the second frame, and a second joint interposed between a lower end of the second frame and an upper end of the third frame.

In claim 6 of the present invention, there is provided the wearable type movement assisting apparatus characterized in that the first joint is provided at a level matching the height of the hip joint of the wearer, wherein the second joint is provided at a level matching the height of the knee joint of the wearer.

In claim 7 of the present invention, there is provided the wearable type movement assisting apparatus characterized in that a first driving source is provided in the first joint for transmitting a driving force for rotating the second frame, wherein a second driving source is provided in the second joint for transmitting a driving force for rotating the third frame.

In claim 8 of the present invention, there is provided the wearable type movement assisting apparatus characterized in that the first and second driving sources include an angle sensor for detecting a joint angle.

In claim 9 of the present invention, there is provided a calibration apparatus of a wearable type movement assisting apparatus for performing calibration whenever a wearer wears a movement assisting wearing device including a driving source generating an assisting power corresponding to biosignals from the wearer by associating the biosignals and the assisting power to a predetermined relationship, the apparatus characterized by comprising: a first storage part for storing a first corresponding relationship between the power and the biosignals generated by the wearer wearing the movement assisting wearing device; and a second storage part for storing a second corresponding relationship between the power and the biosignals generated by the wearer during a process of performing a predetermined basic movement; wherein based on the biosignals generated during the basic movement of the wearer and the second corresponding relationship, a correction of assisting power corresponding to the biosignals is performed for satisfying the first corresponding relationship whenever the movement assisting wearing device is worn by the wearer.

In claim 10 of the present invention, there is provided the calibration apparatus of the wearable type movement assisting apparatus characterized in that the first corresponding relationship includes the power having a positive correlation with respect to the biosignals, wherein the second corresponding relationship includes a relationship between changes of the biosignals and the changes of the power of the basic movement.

In claim 11 of the present invention, there is provided a program for calibration of a wearing type movement assisting apparatus enabling a computer to execute calibration whenever a wearer wears a movement assisting wearing device including a driving source generating an assisting power corresponding to biosignals from the wearer by associating the biosignals and the assisting power to a predetermined relationship, the program characterized by comprising: a first program for enabling the computer to store a first corresponding relationship between the power and the biosignals generated by the wearer wearing the movement assisting wearing device and store a second corresponding relationship between the power and the biosignals generated by the wearer during a process of performing a predetermined basic movement; and a second program for enabling the computer to perform correction of assisting power corresponding to biosignals based on the biosignals generated during the basic movement of the wearer and the second corresponding relationship stored in the second storage part when the movement assisting wearing device is worn by the wearer for satisfying the first corresponding relationship stored in the first storage part.

Effect of the Invention

With the present invention, by detecting a biosignal corresponding to a driving force applied as a load from the driving source and setting a correction value based on the detected signal, no laborious procedures for performing calibration such as attaching weights as a load to the wearer or attaching a coil spring as an alternative to the weights are required. Furthermore, calibration can be automatically executed by using the driving force from the driving source provided in the movement assisting wearing device. Accordingly, the time and effort required for calibration can be reduced significantly. This will further promote putting the wearable type movement assisting apparatus into practical use and popularizing the wearable type movement assisting apparatus.

Furthermore, no unnecessary load for performing calibration is applied to a wearer having weakened muscular strength, and calibration can be automatically performed by mere execution of simple movements by the wearer when the wearer wears the movement assisting wearing device. This enables the correction value to be set according to the state of the wearer and a driving force to be accurately applied to the wearer in cooperation with the movement of the wearer based on the myoelectric potential of the wearer.

Therefore, an assisting force from the driving source can be applied in accordance with the will of the wearer during the execution of calibration. Accordingly, the movement of the wearer can be stably assisted without applying too much or too little assisting force. Thereby, reliability of the wearable type movement can be further improved.

Particularly, the wearer can perform calibration with ease even in a case where manipulation of a worn movement assisting wearing device is considered to be difficult, such as a case where the wearer is a beginner. Therefore, even in a case where the wearer has difficulty in moving freely (such as a physically impaired person), calibration can be performed while avoiding movement difficult for the wearer, and calibration can be performed in a manner complementing the physical deficiencies of the wearer.

BRIEF DESCRIPTION OF DRAWINGS

FIG. 8 is a schematic view of a calibration database 148;

FIG. 22 is a flowchart for describing a control procedure of a reconfiguration calibration performed in correspondence with one motion (single movement); and FIG. 23 is a flowchart for describing a control procedure of a calibration in correspondence with a predetermined reference movement.

EXPLANATION OF REFERENCE NUMERALS

Figure 1:
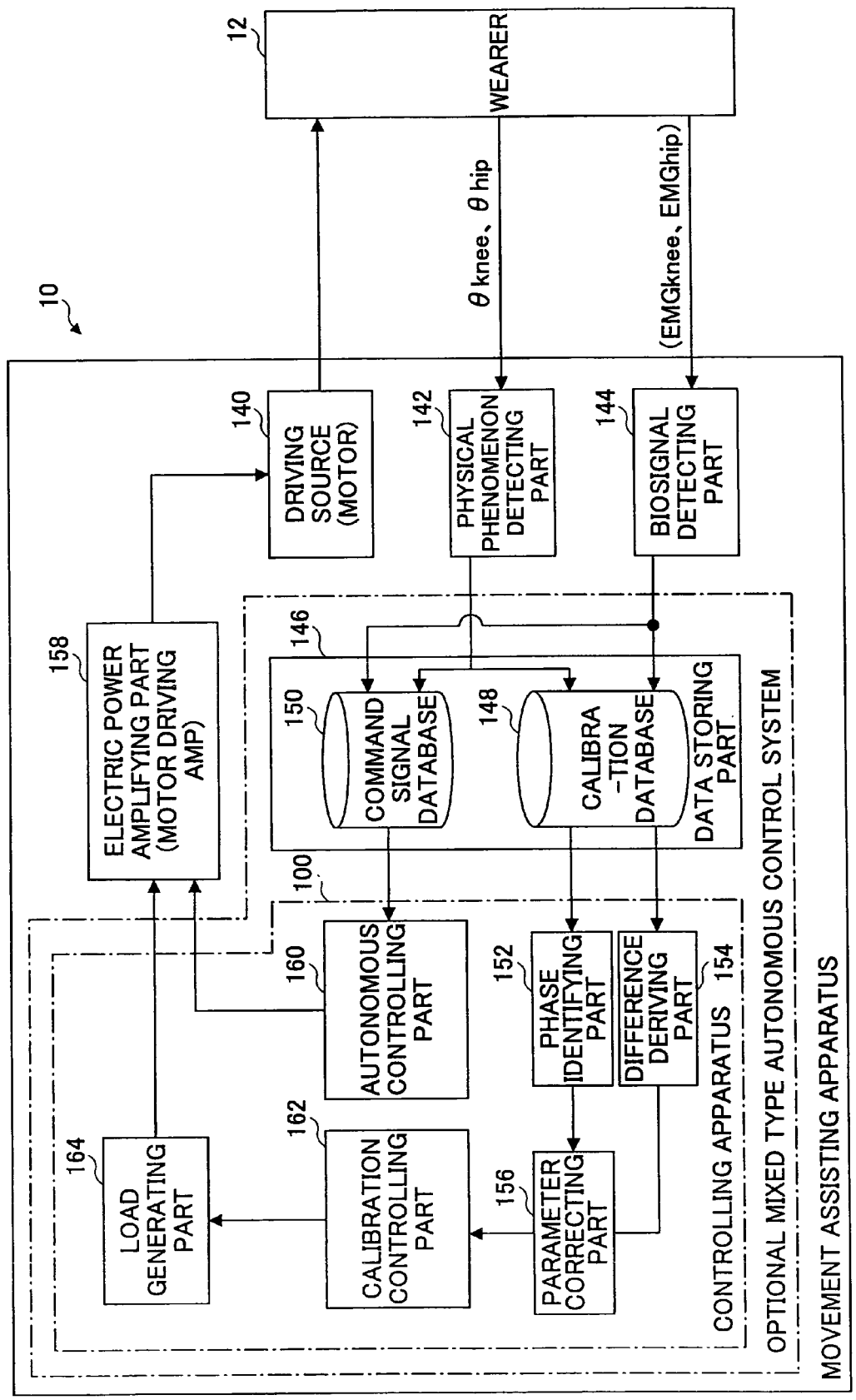
FIG. 1 is a block diagram of a control system applied to a wearable type movement assisting apparatus according to an embodiment of the present invention.

10 movement assisting apparatus
12 wearer
20 right thigh driving motor
22 left thigh driving motor
24 right knee driving motor
26 left knee driving motor 30 waist belt
32, 34 battery
36 control backpack
38a, 38b, 40a, 40b, 42b, 44a, 44b myoelectric potential sensor
50a, 50b, 52a, 52b reaction force sensor
54 right leg assisting part
55 left leg assisting part
56 first frame
58 second frame
60 third frame
62 fourth frame
64 first joint
66 second joint
70, 72, 74, 76 angle sensor
78 first fastening belt
80 second fastening belt
84 heel receiving part
86 electric power circuit
88 input/output interface
100 control apparatus
101-108 difference amplifier
111-114 angle detecting part
121-124 reaction force detecting part
130 memory
140 driving source
142 physical phenomenon detecting part
144 biosignal detecting part
146 data storing part
148 calibration database
150 command signal database
152 phase identifying part
154 difference deriving part
156 parameter correcting part
158 electric power amplifying part
160 controlling part
162 calibration controlling part
164 load generating part

BEST MODE FOR CARRYING OUT THE INVENTION

Next, in order to describe the present invention in more detail, the best mode of the present invention is described with reference to the drawings.

First Embodiment

FIG. 1 is a block diagram showing a control system applied to a wearable type movement assisting apparatus according to an embodiment of the present invention.

As shown in FIG. 1, a control system of a movement assisting apparatus 10 includes a driving source 140 for applying assisting force to a wearer 12, a physical phenomenon detecting part 142 for detecting the joint angle (physical phenomenon) corresponding to the movement of the wearer 12, and a biosignal detecting part 144 for detecting a myoelectric potential (biosignal) corresponding to muscular strength generated by the wearer 12.

A data storing part 146 is loaded with a calibration database 148 for correcting the parameter of a command signal (control signal) according to the detectivity of myoelectric potential (biosignal) corresponding to the muscular strength generated by the wearer 12 and a command signal database 150. It is to be noted that the calibration database 148 includes a first memory space (first storage part) for storing beforehand a first corresponding relationship between a movement force (muscular strength) generated by the wearer 12 wearing the movement assisting wearing device 18 (see FIG. 2, FIG. 3) and a corresponding biosignal (myoelectric potential signal) and a second memory space (second storage part) for storing beforehand a second corresponding relationship between a movement force (muscular strength) generated when the wearer 12 performs a predetermined basic movement and a corresponding biosignal (myoelectric potential signal).

A joint angle (θ knee, θ hip) detected by the physical phenomenon detecting part 142 and a myoelectric potential signal (EMG knee, EMG hip) detected by the biosignal detecting part 144 are input to the calibration database 148 and the command signal database 150.

A controlling apparatus 100 includes a phase identifying part 152, a difference deriving part 154, a parameter correcting part 156, a controlling part 160, a calibration controlling part 162, and a load generating part 164. Furthermore, the calibration controlling part 162 performs correction of assisting power according to biosignals based on a biosignal generated by a basic movement of the wearer 12 and the second corresponding relationship whenever the wearer 12 wears the movement assisting wearing device 18.

That is, when the wearer 12 wears the movement assisting wearing device 18 and switches on its power switch, the calibration control part 162 executes a calibration control process so that the load generating part 164 enables the power amplifying part 158 to apply a driving force of the driving source 140 as a load (input torque) to the wearer 12 step by step and enables the wearer 12 to generate muscular strength for counterbalancing the driving force.

Subsequently, the wearer 12 with the driving force being applied by the driving source 140 performs a predetermined calibration movement (e.g. Task A, a movement of standing up from a sitting state) to generate muscular strength from a skeletal muscle. Along with this calibration movement, the physical phenomenon detecting part 142 detects a joint angle and the biosignal detecting part 144 detects a myoelectric potential signal.

Then, the phase identifying part 152 identifies the phase of the calibration movement of the wearer 12 by comparing the joint angle detected by the physical phenomenon detecting part 142 with a joint angle stored in the calibration database 148.

Furthermore, upon initiation of the calibration controlling process, the difference deriving part 154 compares the load (input torque) of the driving source 140 applied by the load generating part 164 and muscular strength (estimated torque) corresponding to the myoelectric potential signal (measured value) detected by the biosignal detecting part 144, derives the difference between the two, and obtains the above-described second corresponding relationship.

Furthermore, based on the difference between the load (input torque) and muscular strength (estimated torque) obtained by the difference deriving part 154 in correspondence with the phase identified by the phase identifying part 152, the parameter correcting part 156 corrects a parameter K for satisfying the above-described first corresponding relationship.

The reference parameter is not corrected in a case where there is no difference between the input torque applied by the load generating part 164 through the driving source 140 and the muscular strength corresponding to the myoelectric potential signal (measured value) detected by the biosignal detecting part 144. However, in a case where there is a difference between the input torque applied by the load generating part 164 through the driving source 140 and the muscular strength corresponding to the myoelectric potential signal (measured value) detected by the biosignal detecting part 144, the parameter K is corrected so that two of them can match. In such a case, a correction parameter K' is set so that the input torque and the estimated torque may become equal.

Then, the parameter corrected by the parameter correcting part 156 is set as the parameter of the wearer 12 by the calibration controlling part 162 and performs calibration for the next phase.

Accordingly, the driving source 140 is controlled so that an assisting force corresponding to the biosignal detected by the biosignal detecting part 144 can be generated based on the parameter set by the calibration. Thereby, control can be achieved for maintaining a predetermined proportion (for example, 1:1) between muscular strength and assisting force regardless of the daily condition (e.g. resistance value of skin) of the wearer 12 or deviation of the adhered position of the biosignal detecting part 144.

Furthermore, the controlling part 160 obtains the joint angle (θ knee, θ hip) detected by the physical phenomenon detecting part 142 and the myoelectric potential signal (EMG knee, EMG hip) detected by the biosignal detecting part 144, calculates the assisting force of the driving source 140 corresponding to the joint angle and the myoelectric potential signal for each phase by using the correction parameter K' set by the calibration controlling part, and transmits a command signal resulting from the calculation to an electric power amplifying part 158.

Next, an exemplary configuration of the wearing type movement assisting apparatus 10 is described in more detail.

Figure 2:
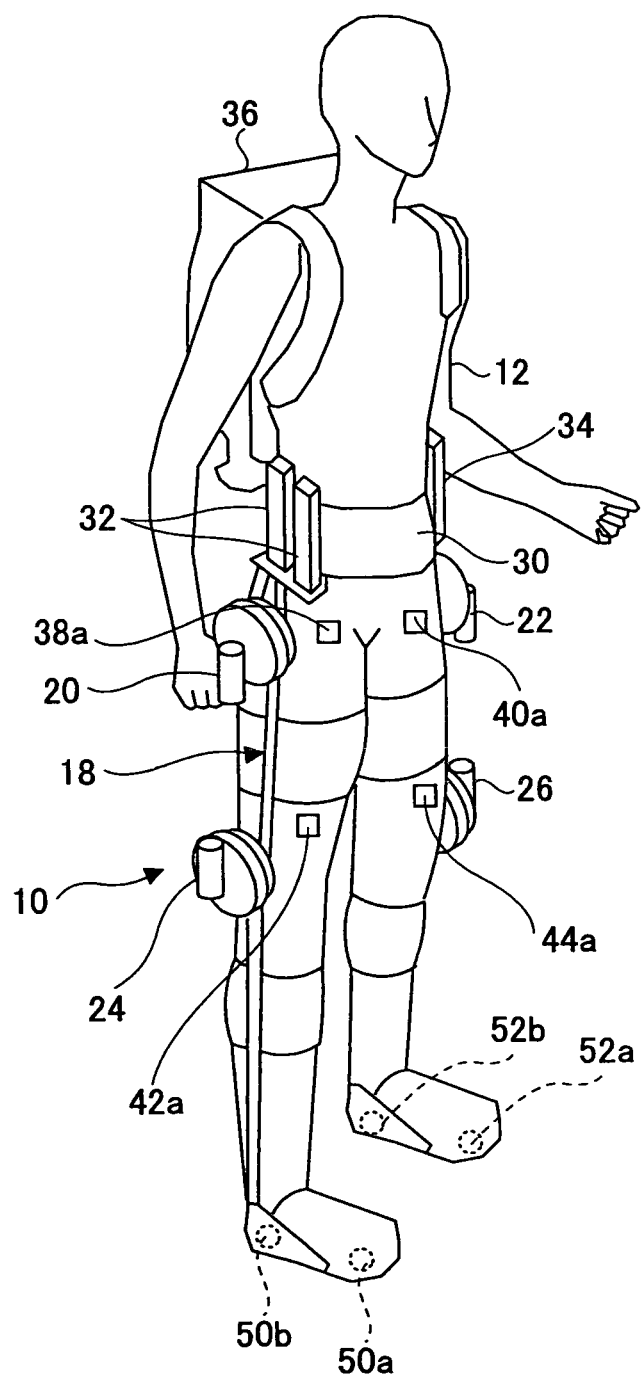
FIG. 2 is a perspective drawing viewed from a front side showing a state where a wearing type movement assisting apparatus is worn according to an embodiment of the present invention.
Figure 3:
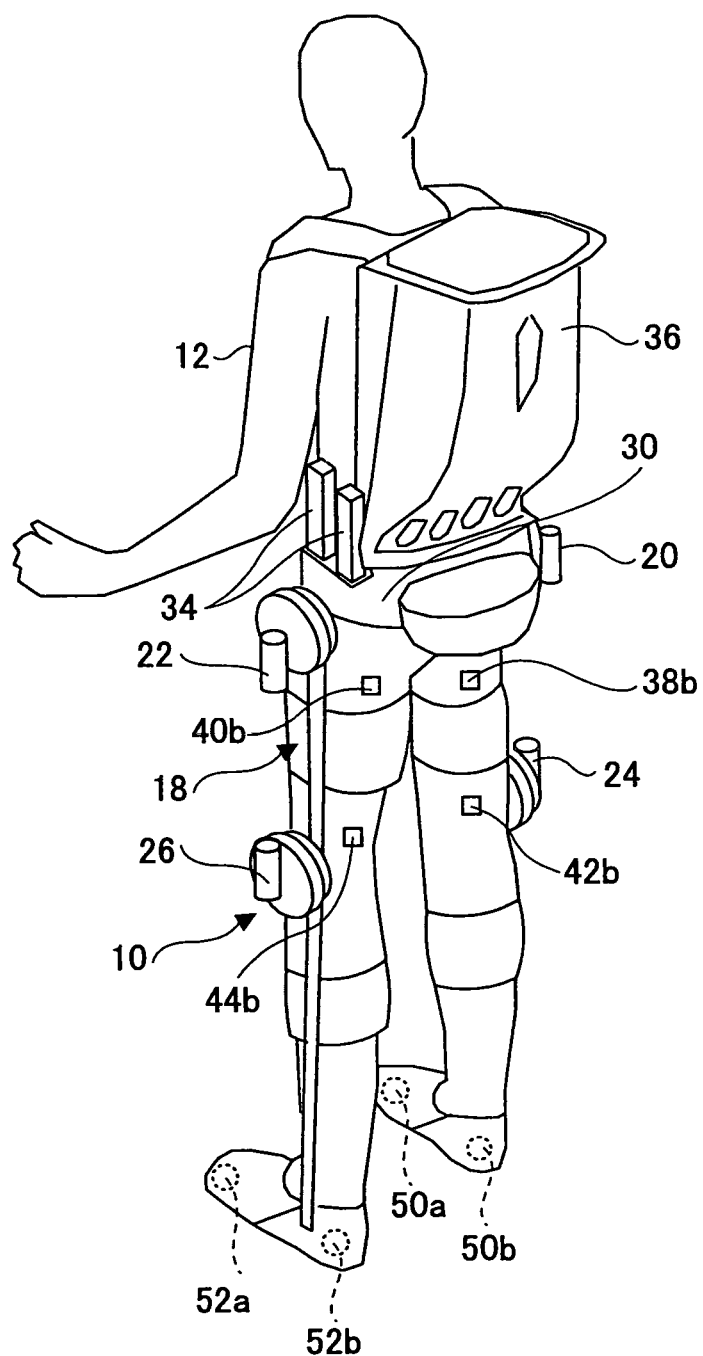
FIG. 3 is a perspective drawing viewed from a rear side showing a state where a wearing type movement assisting apparatus is worn according to an embodiment of the present invention.

FIG. 2 is a front perspective view showing a state where the wearing type movement assisting apparatus according to an embodiment of the present invention is worn. FIG. 3 is a rear perspective view showing the state where the wearing type movement assisting apparatus according to an embodiment of the present invention is worn.

As shown in FIGS. 2 and 3, the movement assisting apparatus 10 is for assisting with a walking movement for those having difficulty in walking by themselves, for example, a leg-impaired person unable to walk freely due to deterioration of muscular strength of skeletal muscles or a patient undergoing walking rehabilitation. The movement assisting apparatus 10 detects biosignals (surface myoelectric potential) created upon generating muscular strength according to signals from the brain and operates to apply a driving force from an actuator based on the detected signals.

Therefore, the movement assisting apparatus 10 is completely different from a so-called playback type robot that controls a robot hand with a computer according to predetermined input data, and is also referred to as a robot suit or a powered suit.

When the wearer 12 wearing the movement assisting apparatus 10 performs a walking movement according to his/her own will, the movement assisting apparatus 10 applies a driving torque corresponding to a biosignal generated upon performing the walking movement as an assisting force, to thereby achieve, for example, walking by using half of the muscular strength normally required for walking. Therefore, the wearer 12 is able to support his/her entire weight and walk owing to the combination of his/her own muscular strength and the driving torque from the actuator (in this embodiment, an electric powered driving motor is used).

In such a case, the movement assisting apparatus 10 is controlled so that the assisting force (motor torque) according to the shift of barycenter along with the walking movement (described below) reflects the will of the wearer 12. Therefore, the actuator of the movement assisting apparatus 10 is controlled so as not to apply load that is contrary to the will of the wearer 12 and not to obstruct the movement of the wearer 12.

Furthermore, the movement assisting apparatus 10 can assist movement other than the walking movement, such as a movement in which the wearer 12 stands up from a state of sitting on a chair, or a movement in which the wearer 12 sits down from a state of standing up. Furthermore, the wearer 12 can be assisted with power when the wearer 12 climbs up or down a staircase. Although the movement of climbing up a staircase or standing up from a chair may be difficult for one having low muscular strength, a wearer 12 wearing the movement assisting apparatus 10 can move without worrying about his/her lowered muscular strength by being supplied with driving torque in accordance with his/her own will.

Next, an exemplary configuration of the movement assisting apparatus 10 is described.

As shown in FIGS. 2 and 3, the movement assisting apparatus 10 has an actuator (corresponding to driving source 140) included in the movement assisting wearing device 18 worn by the wearer 12. The actuator includes a right thigh driving motor 20 located at the right hip joint of the wearer 12, a left thigh driving motor 22 located at the left hip joint of the wearer 12, a right knee driving motor 24 located at the right knee joint of the wearer 12, and a left knee driving motor 26 located at the left knee joint of the wearer 12. These driving motors 20, 22, 24, 26 are driving sources including servo motors having their driving torques controlled by control signals from the controlling apparatus and include a deceleration mechanism (not shown) for decelerating the motor rotation to a predetermined deceleration ratio. Although the driving motors 20, 22, 24, 26 are small, they can apply a sufficient driving force.

Furthermore, batteries 32, 34 which function as a power source for driving the driving motors 20, 22, 24, 26 are attached to a waist belt 30 worn around the waist of the wearer 12. The batteries 32, 34 are rechargeable batteries and are separately arranged on the left and right so as not to obstruct the walking movement of the wearer 12.

Furthermore, a control backpack 36 mounted on the back of the wearer 12 contains, for example, a controlling apparatus, a motor driver, a measuring apparatus, and a power circuit (described below). It is to be noted that the lower part of the control backpack 36 is supported by the waist belt 30 and is mounted in a manner in which the weight of the control backpack 36 does not burden the wearer 12.

Furthermore, the movement assisting apparatus 10 includes myoelectric potential sensors 38a, 38b for detecting surface myoelectric potential (EMG hip) corresponding to the movement of the right thigh of the wearer 12, myoelectric potential sensors 40a, 40b for detecting surface myoelectric potential (EMG hip) corresponding to the movement of the left thigh of the wearer 12, myoelectric potential sensors 42a, 42b for detecting surface myoelectric potential (EMG knee) corresponding to the movement of the right knee, and myoelectric potential sensors 44a, 44b for detecting surface myoelectric potential (EMG knee) corresponding to the movement of the left knee.

Each of these myoelectric potential sensors 38a, 38b, 40a, 40b, 42a, 42b, 44a, and 44b is a detecting part for measuring the surface myoelectric potential created during the generation of muscular strength of the skeletal muscles and includes an electrode (not shown) for detecting slight potential generated in the skeletal muscles. It is to be noted that, in this embodiment, each of these myoelectric potential sensors 38a, 38b, 40a, 40b, 42a, 42b, 44a, and 44b is attached by adhering an adhesive seal that covers the area surrounding the electrode onto the surface of the skin of the wearer 12.

In a human body, a synaptic transmission substance of acetylcholine is released to the surface of the muscles forming the skeletal muscles according to commands from the brain. As a result, the ion permeability of the sarcolemma changes, to thereby generate action potential (EMG: Electro MyoGram Myoelectricity). Accordingly, the action potential causes retraction of the sarcolemma and generates muscular strength. Accordingly, the muscular strength generated during the walking movement can be estimated by detecting the myoelectric potential of the skeletal muscles. Based on the estimated muscular strength, the assisting force required for the walking movement can be obtained.

Furthermore, although muscles expand and contract when blood supplies a protein called actin and myosin, the muscular strength is generated when the muscles contract. In a joint where two bones are rotatably joined together, a flexor for generating a force in a bending direction of the joint and an extensor for generating a force in an extending direction are provided between two bones.

Furthermore, in a human body, there are plural muscles below the waist for moving the legs, such as the musculi iliopsoas for raising the thighs forward, the musculus gluteus maximus for lowering the thighs, the quadriceps for extending the knees, and the biceps femoris for bending the knees.

The myoelectric potential sensors 38a, 40a, which are adhered to the front proximal part of the thigh of the wearer 12, measure the myoelectric potential corresponding to the muscular strength generated when the leg is delivered forward by detecting the surface myoelectric potential of the musculi iliopsoas.

The myoelectric potential sensors 38b, 40b, which are adhered to the hip of the wearer 12, measure the myoelectric potential corresponding to the muscular strength generated, for example, when kicking the leg behind or climbing a staircase by detecting the surface myoelectric potential of the musculus gluteus maximus.

The myoelectric potential sensors 42a, 44a, which are adhered to the front side above the knees of the wearer 12, measure the myoelectric potential corresponding to the muscular strength generated when delivering the part below the knees forward by detecting the surface myoelectric potential of the quadriceps.

The myoelectric potential sensors 42b, 44b, which are adhered to the rear side above the knees of the wearer 12, measure the myoelectric potential corresponding to the muscular strength generated when retracting the part below the knees backward by detecting the surface myoelectric potential of the biceps femoris.

Accordingly, in the movement assisting apparatus 10, the driving current to be supplied to four driving motors 20, 22, 24, and 26 are obtained based on the surface myoelectric potential detected by these myoelectric potential sensors 38a, 38b, 40a, 40b, 42a, 42b, 44a, and 44b. By driving the driving motors 20, 22, 24, and 26 with the driving current, assisting force is applied for supporting the walking movement of the wearer 12.

Furthermore, it is necessary to detect the load applied to the feet for performing the shift of barycenter caused by the walking movement. Therefore, reaction force sensors 50a, 50b, 52a, 52b (shown with broken lines in FIGS. 2 and 3) are provided on the backs of the left and right feet of the wearer 12.

Furthermore, the reaction force sensor 50a detects the reaction force against the load of the front of the right foot, and the reaction force sensor 50b detects the reaction force against the load of the rear of the right foot. The reaction force sensor 52a detects the reaction force against the load of the front of the left foot, and the reaction force sensor 52b detects the reaction force against the load of the rear of the left foot. Each reaction force sensor 50a, 50b, 52a, and 52b including, for example, a piezoelectric element is able to detect changes of load in correspondence with weight shift and detect whether the foot of the wearer 12 is contacting the ground.

Next, a configuration of the movement assisting wearing device 18 is described with reference to FIGS. 4 and 5.

Figure 4:
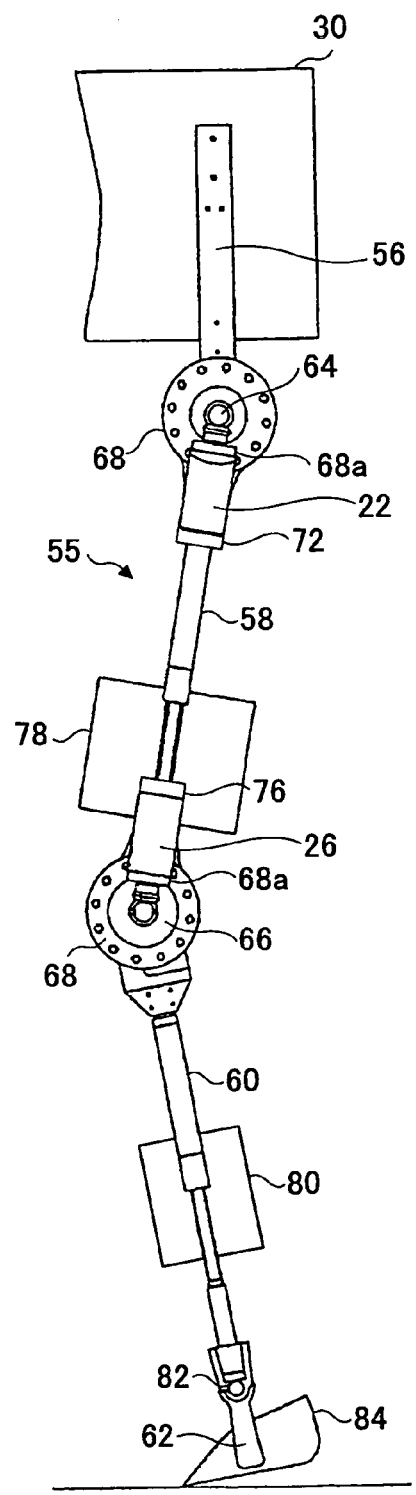
FIG. 4 is a left side view of a movement assisting wearing device 18.

FIG. 4 is a left side view of the movement assisting wearing device 18. FIG. 5 is a rear view of the movement assisting wearing device 18.

Figure 5:
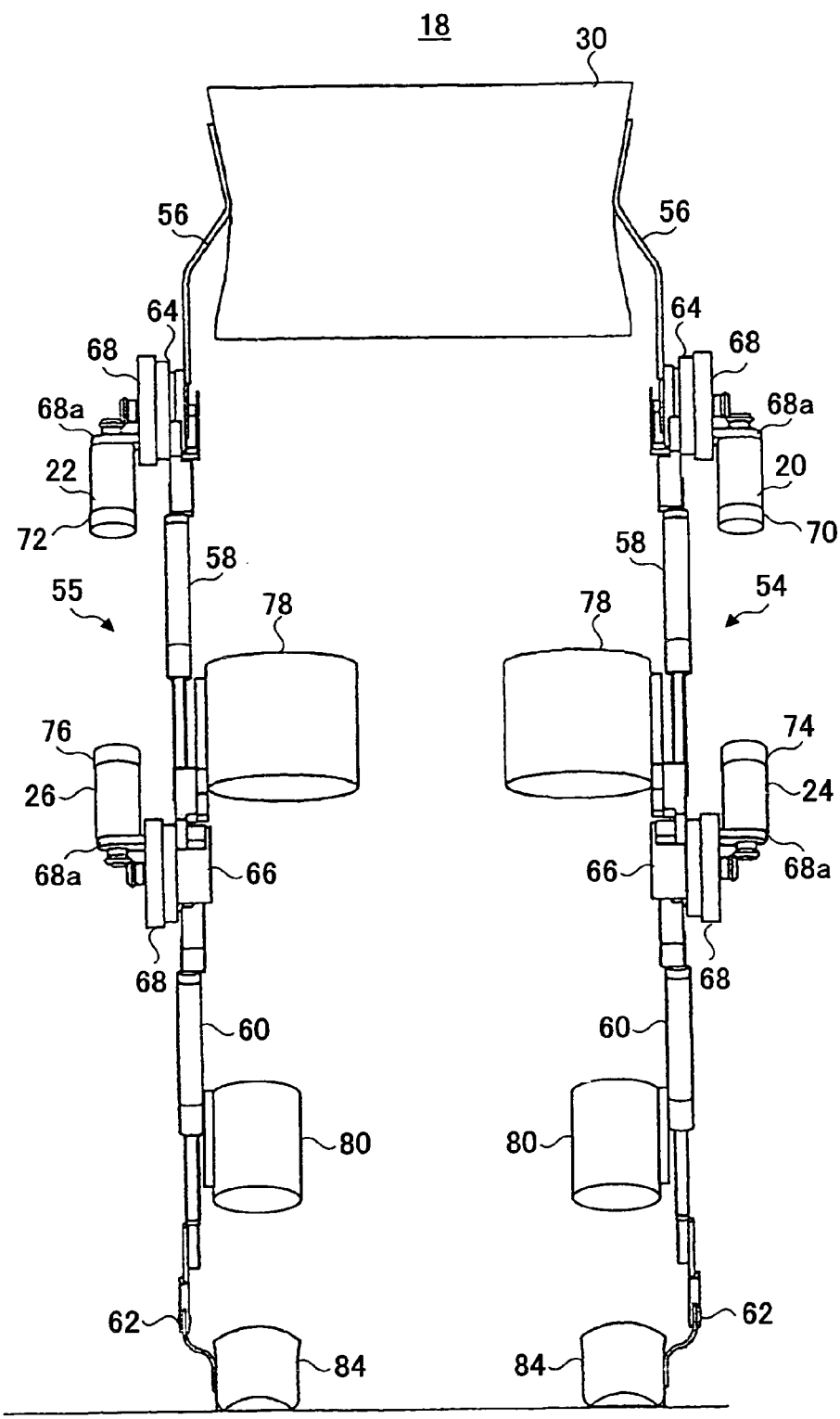
FIG. 5 is a rear view of a movement assisting wearing device 18.

As shown in FIGS. 4 and 5, the movement assisting wearing device 18 includes the waist belt 30 worn around the waist of the wearer, a right leg assisting part 54 provided at the right side below the waist belt 30, and a left leg assisting part 55 provided at the left side below the waist belt 30.

The right leg assisting part 54 and the left leg assisting part 55 are arranged symmetrical to each other, in which each includes a first frame 56 extending below the waist belt 30 for supporting the waist belt 30, a second frame 58 extending below the first frame 56 and formed along the outer side of the thigh of the wearer 12, a third frame 60 extending below the second frame 58 and formed along the outer side of the shin of the wearer 12, and a fourth frame 62 on which the bottom side of the foot (shoe sole when a shoe is worn) of the wearer 12 is placed.

A first joint 64 having a bearing structure is disposed between a lower end of the first frame 56 and an upper end of the second frame 58 for rotatably connecting the first frame 56 and the second frame 58. The first joint 64 is disposed at a level matching the height of the hip joint. The first frame 56 is connected to the supporting side of the first joint 64, and the second frame 58 is connected to the rotating side of the first joint 64.

Furthermore, a second joint 66 having a bearing structure is disposed between a lower end of the second frame 58 and an upper end of the third frame 60 for rotatably connecting the second frame 58 and the third frame 60. The second joint 66 is disposed at a level matching to the height of the knee joint. The second frame 58 is connected to the supporting side of the second joint 66, and the third frame 60 is connected to the rotating side of the second joint 64.

Therefore, the second frame 58 and the third frame 60 are attached in a manner being able to oscillate having the first joint 64 and the second joint 66 as fulcrums of rotation with respect to the first frame 56 fixed to the waist belt 30. That is, the second frame 58 and the third frame 60 are configured to perform the same movements as the corresponding leg of the wearer 12.

Furthermore, motor brackets 68 are provided at the supporting sides of the first joint 64 and the second joint 66. The motor bracket 68 includes a motor supporting part 68a protruding outward in a horizontal direction. The driving motor 20, 22, 24, 26 is attached to the motor supporting part 68a in a vertical state. Thus, the driving motor 20, 22, 24, 26 is provided in a manner without having to protrude too far to the side so as to avoid contacting surrounding obstacles during the walking movement.

Furthermore, the first joint 64 and the second joint 66 are configured to allow a rotary shaft of the driving motors 20, 22, 24, 26 to transmit a driving torque to the second frame 58 and the third frame 60 (drive-receiving side) via a gear.

Furthermore, the drive motors 20, 22, 24, 26 include an angle sensor 70, 72, 74, 76 (corresponding to physical phenomenon detecting part 142) for detecting a joint angle. The angle sensor 70, 72, 74, and 76 includes, for example, a rotary encoder that counts pulses in proportion to the joint angle of the first joint 64 and the second joint 66, and outputs electric signals (as sensor output) in accordance with the number of pulses corresponding to the joint angle.

The angle sensor 70, 72 detects the rotation angle between the first frame 56 and the second frame 58 which correspond to the joint angle (θ hip) of the hip joint of the wearer 12. Furthermore, the angle sensor 74, 76 detects the rotation angle between the second frame 58 and the third frame 60 which corresponds to the joint angle (θ knee) of the knee joint of the wearer 12.

It is to be noted that the first joint 64 and the second joint 66 are configured to rotate within the range in which the hip joint and the knee joint of the wearer 12 can rotate. The first joint 64 and the second joint 66 have installed a stopping mechanism (not shown) for preventing excessive movement of the hip joint and the knee joint of the wearer 12.

The second frame 58 has attached a first fastening belt 78 which is to be fastened to the thigh of the wearer 12. Furthermore, the third frame 60 has attached a second fastening belt 80 which is to be fastened to a part below the knee of the wearer 12. Accordingly, the driving torque generated by the driving motors 20, 22, 24, 26 is transmitted to the second frame 58 and the third frame 60 via a gear and is further transmitted as assisting force to the leg of the wearer 12 via the first fastening belt 78 and the second fastening belt 80.

Furthermore, a fourth frame 62 is rotatably connected to a lower end of the third frame 60 via an axle 82. Furthermore, a heel receiving part 84 is provided to a lower end of the fourth frame 62 for placing the heel part of the shoe sole of the wearer 12 thereon. Moreover, the second frame 58 and the third frame 60 can have their lengths in the axle direction adjusted by a screw mechanism so that the length can be adjusted in correspondence with the length of the leg of the wearer 12.

Each frame 56, 58, 60, 64 is formed by metal and is configured to support the weight of the batteries 32, 34 provided in the waist belt 30, the control backpack 36, and the movement assisting wearing device 18. That is, the movement assisting apparatus 10 is configured to prevent the weight of the movement assisting wearing device 18, etc., from affecting the wearer 12 and is attached in a manner preventing the wearer 12 having weakened muscles from having an unnecessary load applied.

Figure 6:
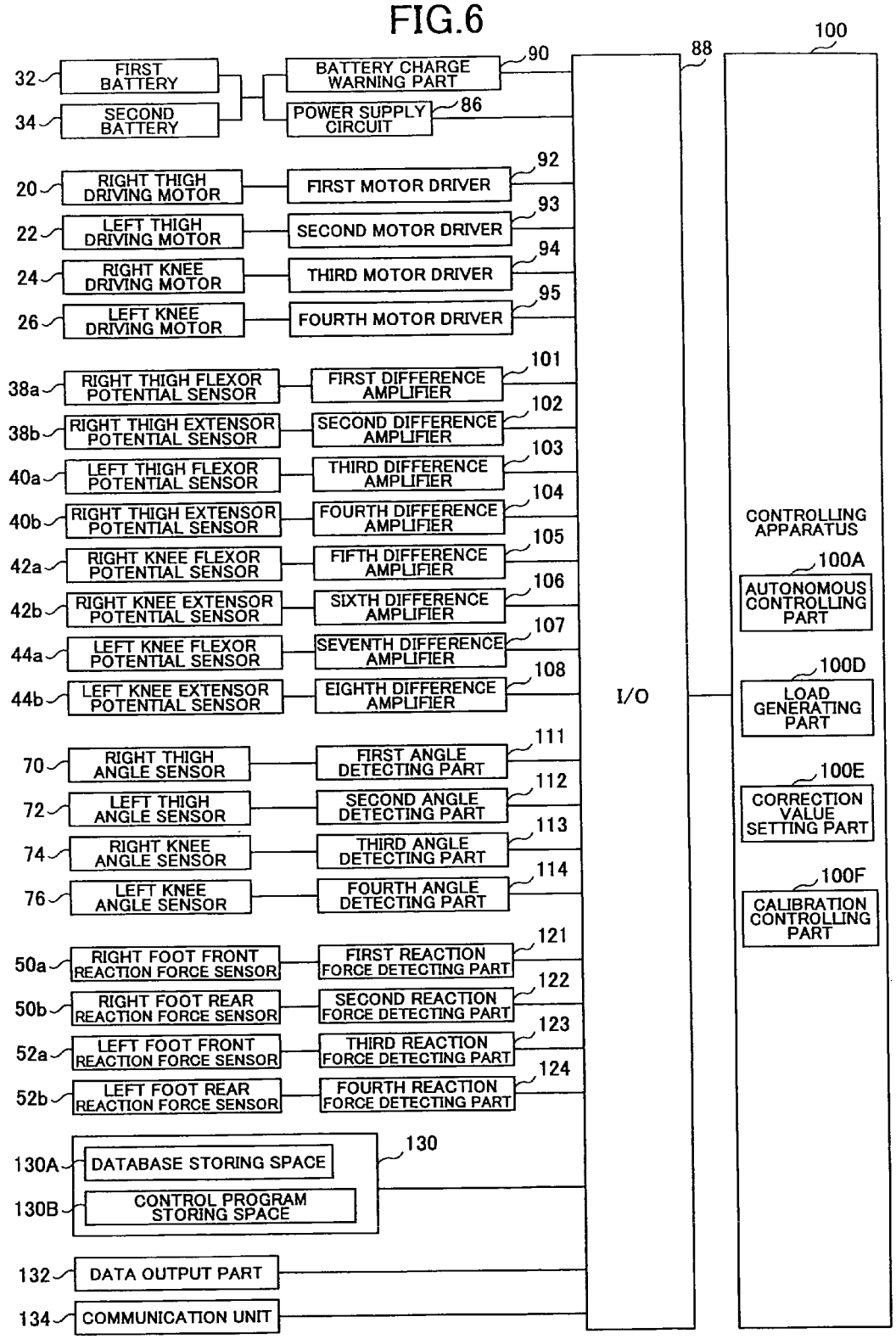
FIG. 6 is a block diagram of each component of a movement assisting apparatus 10.

FIG. 6 is a block diagram of respective components included in the movement assisting apparatus 10. As shown in FIG. 6, the batteries 32, 34 supply electric power to a power supply circuit 86. The power supply circuit 86 converts the power to a predetermined voltage and supplies constant voltage to an input/output interface 88. Furthermore, the charge capacity of the batteries 32, 34 is monitored by a battery charge warning part 90. The battery charge warning part 90 outputs a warning when the remaining charge capacity becomes less than a predetermined amount to inform the wearer 12 to exchange or charge the batteries.

The first-fourth motor drivers 92-95, which drive driving motors 20, 22, 24, 26, respectively, amplify the driving voltages corresponding to the control signals from the controlling apparatus 100 via the input/output interface 88 and output the driving voltages to the driving motors 20, 22, 24, and 26.

The detection signals of the surface myoelectric potential output from each myoelectric potential sensor 38a, 38b, 40a, 40b, 42a, 44a, 44b are amplified by the first-eighth difference amplifiers (corresponding to electric power amplifying part 158) 101-108, then converted into digital signals by an A/D converter (not shown), and then input to the controlling apparatus 100 via the input/output interface 88. It is to be noted that the myoelectric potential generated by muscles is slight. Therefore, in order for the first-eighth difference amplifiers 101-108 to amplify the myoelectric potential (e.g. 30 μV) to a voltage distinguishable by a computer (e.g. approximately 3 V), a gain of 100 dB ($10^5$) is required.

Furthermore, the angle detection signals output from the angle sensors 70, 72, 74, 76 are input to corresponding first-fourth angle detecting parts 111-114, respectively. The first-fourth angle detecting parts 111-114 convert the detected pulses into angle data values corresponding to angles by using a rotary encoder and input the detected angle data to the controlling apparatus 100 via the input/output interface 88.

The reaction force detection signals output from the reaction force sensors 50a, 50b, 52a, 52b are input to corresponding first-fourth reaction force detecting parts 121-124, respectively. The first-fourth reaction force detecting parts 121-124 convert the detected voltages into digital values corresponding to force by using the piezoelectric elements and input the detected reaction force data to the controlling apparatus 100 via the input/output interface 88.

A memory (corresponding to the data storing part 146) 130 is a storing part for storing respective data therein. The memory 130 includes, for example, a database storing space 130A for storing control data in units of phases corresponding to each movement pattern (task) such as a standing movement, a walking movement, or a sitting movement, and a control program storing space 130B for storing control programs for controlling each motor.

In this embodiment, the calibration database 148 and the command signal database 150 are stored in the database storing space 130A. Furthermore, as shown in FIG. 8, the calibration database 148 stores the first corresponding relationship between the muscular strength (power) $e_{A1}(t)$ ... and the biosignal $E_{A1}(t)$ ... generated by the wearer 12 wearing the movement assisting wearing device 18, and the reference parameter $K_{A1}$ .... Furthermore, in the first corresponding relationship, the muscular strength $e_{A1}(t)$ ... and the biosignal $E_{A1}(t)$ ... form a proportional relationship and have a positive correlation.

Furthermore, the calibration database 148 stores the second corresponding relationship between the muscular strength (power) $e'_{A1}(t)$ ... and the biosignal $E_{A1}(t)$ ... generated during a process where the wearer 12 performs a predetermined basic movement, and the correction parameter $K'_{A1}$ .... The second corresponding relationship is a relationship between the changes of biosignal $E_{A1}(t)$ ... and the changes of the muscular strength (power) $e_{A1}(t)$ ... during a basic movement.

Furthermore, the control data output from the controlling apparatus 100 are output to a data outputting part 132 and a communication unit 134 via the input/output interface 88 for displaying on a monitor (not shown) or transferring to a data monitoring computer (not shown) by data communication, for example.

Furthermore, the controlling apparatus 100 includes an autonomous controlling part 100A (corresponding to controlling part 160) which compares the joint angle detected by the angle sensor 70, 72, 74, 76 and the joint angle of the reference parameter to identify the phase of the movement pattern of the wearer 12 and generates a command signal for generating power corresponding to the phase.

Furthermore, the controlling apparatus 100 includes: a load generating part 100D which applies a predetermined driving force from the driving motor (driving source) 20, 22, 24, 26 as an external load; a correction value setting part 100E (corresponding to parameter correcting part 156) which detects a biosignal generated in response to the applied driving force with a myoelectric potential sensor (detecting part) 38a, 38b, 40a, 40b, 42a, 42b, 44a, 44b, generates a parameter (for example, proportion gain in proportional control) for calculation by the autonomous controlling part 100A based on the detected signal, and sets the parameter as the unique correction value of the wearer; and a calibration controlling part 100F which controls the movement of, for example, the correction value setting part 100E to set the corrected parameter as the unique parameter of the wearer 12.

Calibration in this embodiment includes, for example, a default calibration which is performed when the movement assisting wearing device 18 is worn for the first time (e.g. upon purchase) and a reconfigured calibration which is performed each time the movement assisting wearing device 18 is worn after the default calibration.

In the default calibration, a correction value setting process is performed by having the wearer 12 remain motionless in a predetermined position (described below).

Furthermore, the reconfigured calibration includes, for example, motionless state calibration where a correction value updating process is executed by having the wearer 12 generate muscular strength in a motionless state or one motion calibration where a correction value updating process is executed by having a standing wearer 12 bend and stretch his/her knees once from a knee bent state.

In performing the calibration, the load applied to the wearer 12 is initially set to be a small load and is gradually increased along with the progression of calibration operations by controlling the driving motors 20, 22, 24, and 26 and detecting the biosignals generated in response to the driving forces of the driving motors 20, 22, 24, and 26. Furthermore, in the wearable type movement assisting apparatus 10 of this embodiment, it is possible to select either one of the calibration executed as a default calibration in a motionless state and a reconfiguration calibration executed as a one motion calibration each time the wearable type movement assisting apparatus 10 is worn.

Figure 7:
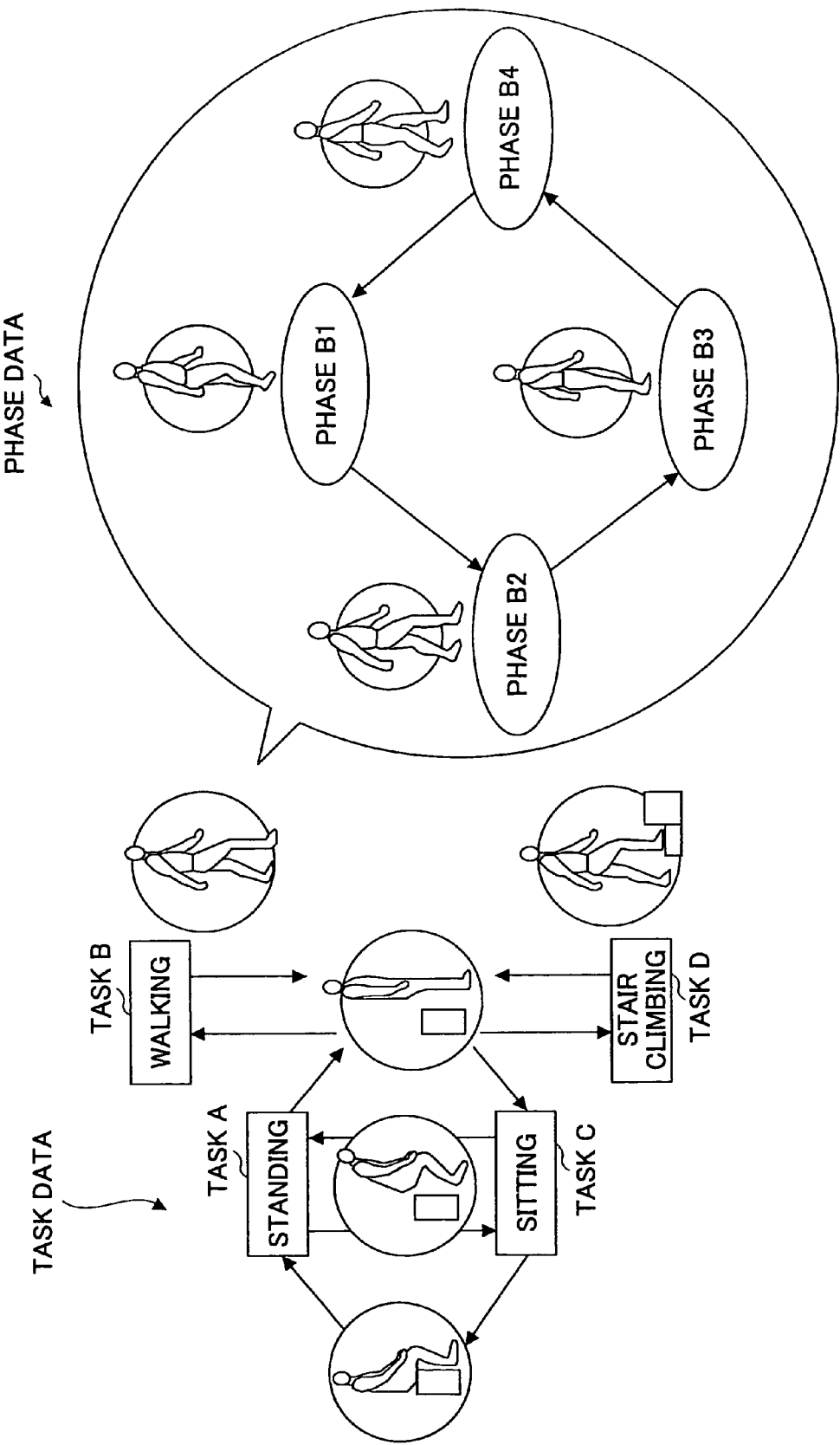
FIG. 7 is a diagram showing examples of respective tasks and phases.
Figure 9:
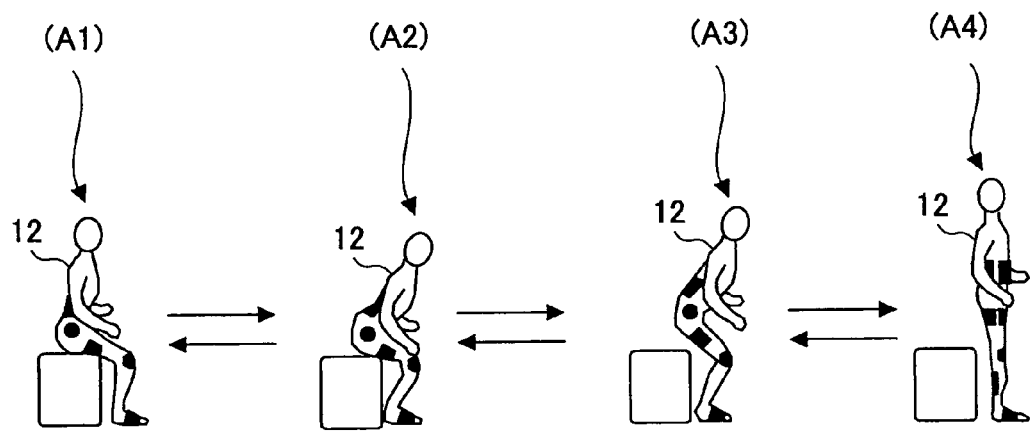
FIG. 9 is a diagram showing a movement process of phases A1-A4 as an example of movement.

Next, an operation during performing calibration by the wearer 12 is described with reference to FIGS. 7-9. FIG. 7 is a schematic diagram showing an example of each task and phase stored in each database.

As shown in FIG. 7, the tasks which categorize the movements of the wearer 12 are stored in memory 130, for example, task A including data of a standing movement where the wearer 12 transitions from a sitting state to a standing state, task B including data of a walking movement where the wearer 12 walks from a standing state, task C including data of a sitting movement where the wearer 12 transitions from a standing state to a sitting state, and task D including data of a stair climbing movement where the wearer 12 transitions from a standing state to a stair climbing state.

Furthermore, plural phase data defining the minimum unit of movement are set to each task. For example, in a case of a walking movement of task B, there is stored a phase B1 including movement data of a state where both legs are aligned, a phase B2 including movement data of a state where the right leg is brought forward, a phase B3 including movement data of a state where the left leg is brought forward to align it with the right leg, and a phase B4 including movement data of a state where the left leg is brought forward before the right leg.

FIG. 8 is a schematic view showing a calibration database 148.

As shown in FIG. 8, the calibration database 148 stores, for example, the surface myoelectric potential $e_{A1}(t)$ . . . detected according to each phase divided in correspondence with each task A, B, . . . , and the reference parameter $K_{A1}$ . . . corresponding to the myoelectric potential.

In this embodiment, the wearer 12 wearing the movement assisting wearing device 18 performs a predetermined calibration operation. For example, as shown in FIG. 9, the wearer 12 performs a movement of standing up from a sitting state (phase A1-A4) as a basic movement and then performs a movement of sitting back down (phase A4-A1).

Next, a calibration principle of the biosignal detecting part 144, which detects the myoelectric potential corresponding to the muscular strength generated by the wearer 12, is described in more detail.

In a case where the wearer 12 makes a subtle movement, the relationship between the surface myoelectric potential and the muscular strength generated by the wearer 12 is substantially linear. Accordingly, there is a method developed for estimating the torque generated by the wearer 12 based on the surface myoelectric potential measured by the following formulas (1) and (2).

It is to be noted that the estimated torque is referred to as "virtual torque".

$$\tau_{hip} = K_1 e_1 - K_2 e_2 \tag{1}$$

$$\tau_{knee} = K_4 e_4 - K_3 e_3 \tag{2}$$

Figure 10:
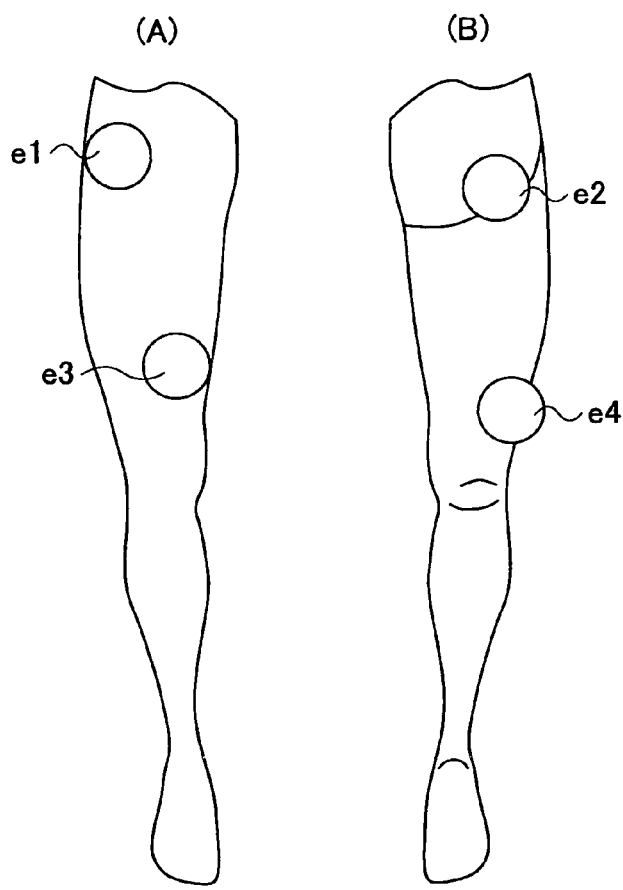
FIG. 10 are diagrams for showing a detection position of surface myoelectric potential $e_1$-$e_4$, in which (A) is a diagram viewing a leg from the front and (B) is a diagram viewing a leg from the rear.
Figure 11:
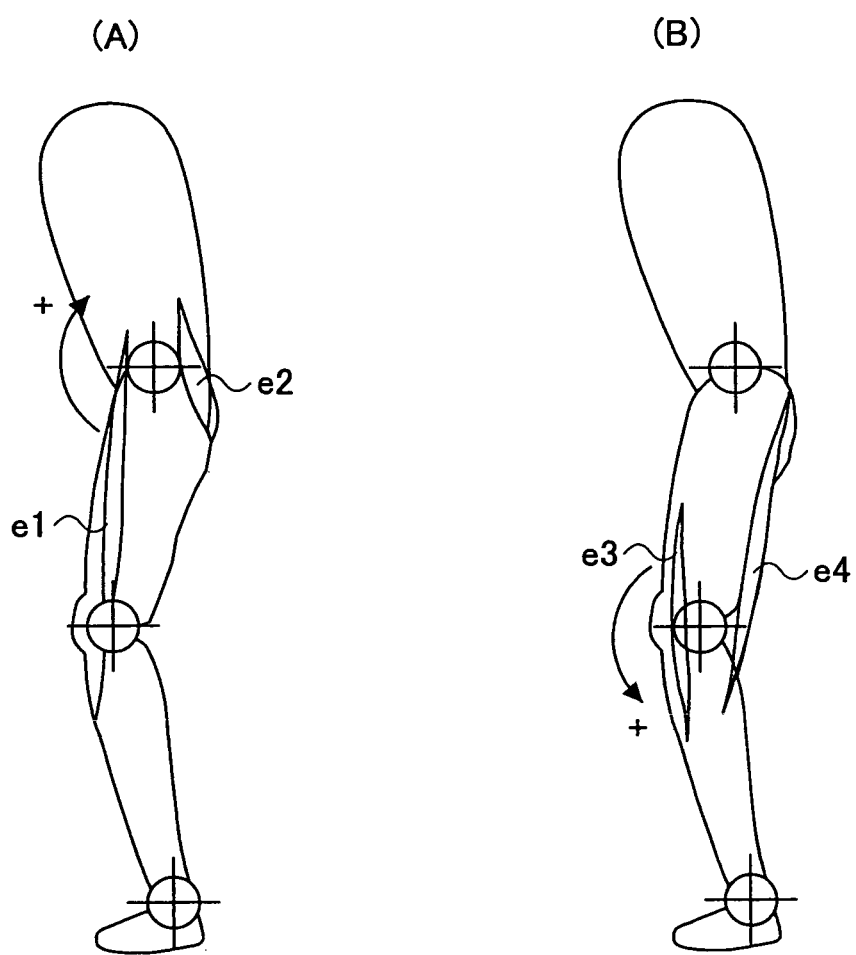
FIG. 11 are diagrams for showing a detection position of surface myoelectric potential $e_1$-$e_4$, in which (A) is a side view of a leg for showing surface myoelectric potential when bending the hip joint in the arrow direction and (B) is a side view of a leg for showing surface myoelectric potential when bending the knee joint in the arrow direction.

In the formulas (1) and (2), "$\tau_{hip}$" indicates the virtual torque of the hip joint, "$\tau_{knee}$" indicates the virtual torque of the knee joint, "$e_1$-$e_4$" indicate the surface myoelectric potential generated by muscles, and "$K_1$-$K_4$" indicate parameters. The hip joint and the knee joint of the wearer 12 are moved according to the balance of expansion and contraction of the flexor and extensor. As shown in FIG. 10(A) (B) and FIG. 11(A) (B), "$e_1$" indicates the surface myoelectric potential of the rectus femoris, "$e_2$" indicates the surface myoelectric potential of the musculus gluteus maximus, "$e_3$" indicates the surface myoelectric potential of the musculus vastus medialis, and "$e_4$" indicates the surface myoelectric potential of the biceps femoris.

In the calculation of virtual torque, the values filtered through a digital filter are used taking noise into consideration. In this embodiment, the values filtered through a low pass filter are obtained as the values of the surface myoelectric potential.

In the calibration of the control system for detecting surface myoelectric potential, each parameter K of the next Formula (3) extracts the virtual torque of the corresponding muscle by the Formulas (1) and (2).

$$\tau = Ke \tag{3}$$

That is, in the calibration of this embodiment, the value of the parameter K of Formula (3) is calculated so that the value of the surface myoelectric potential becomes 1 when the power generated by a target muscle is 1 Nm. This value is updated.

Accordingly, in this embodiment, either in a case of the default calibration or the reconfiguration calibration, the value of the above-described parameter is corrected by using the detection results of the myoelectric potential sensors 38a, 38b, 40a, 40b, 42a, 42b, 44a, 44b.

Next, the reconfiguration calibration is described. This calibration can be applied to a single motion where the wearer 12 in a sitting state moves his/her knees from a bent state to an extending state, can reduce the load of the wearer 12, and can complete calibration in a short time.

Figure 12:
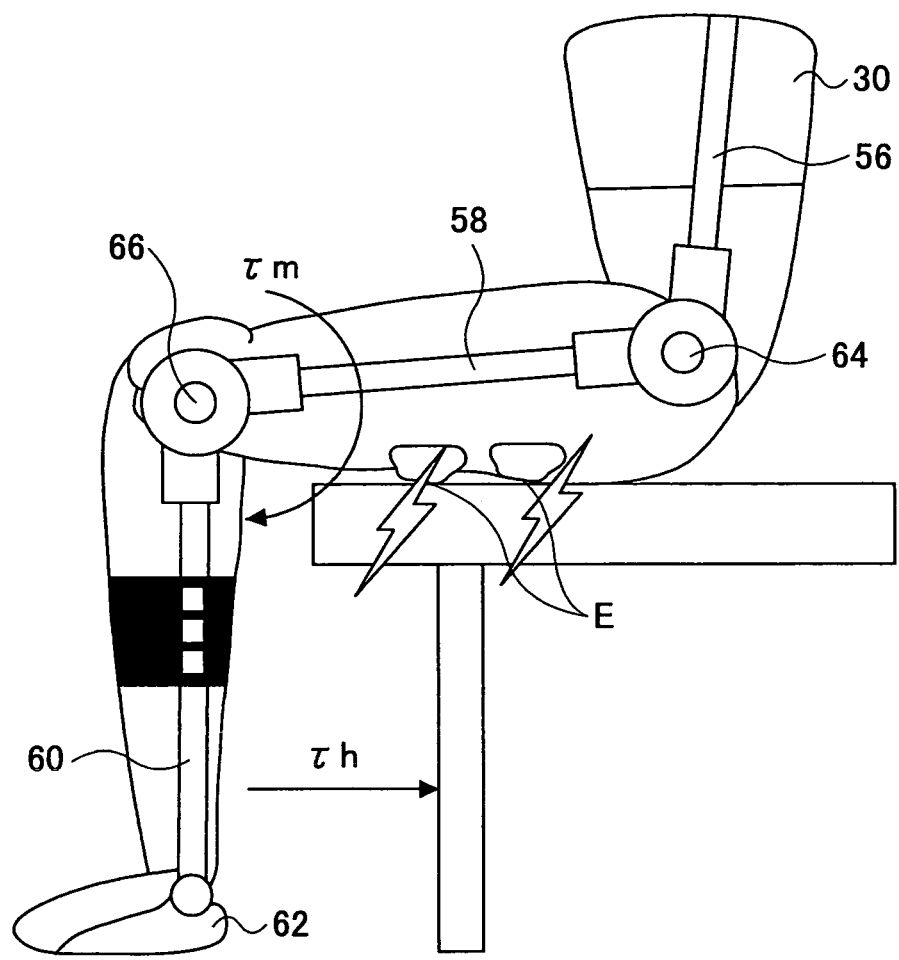
FIG. 12 is a schematic view for showing a state of a flexor of a knee joint of a wearer 12 wearing a movement assisting wearing device 18.

FIG. 12 is a schematic view showing the state of a flexor of a knee joint of the wearer 12 wearing the movement assisting wearing device 18.

As shown in FIG. 12, in a state where the movement assisting wearing device 18 is worn by the wearer 12, an input torque $\tau_m$ is applied as a load to the knee joint by using the driving motors 20, 22, 24, 26. The wearer 12 maintains a motionless state of not moving the knee joint by applying muscular strength for counterbalancing the input torque $\tau_m$. In such a state, it can be said that the input torque $\tau_m$ applied from the driving motors 20, 22, 24, 26 and the muscular strength $\tau_h$ generated by the wearer 12 are equal.

Accordingly, the following Formula (4) can be satisfied.

$$\tau_m(t)=\tau_h(t) \quad (4)$$

Since the muscular strength generated by the wearer 12 according to Formula (3) can be indicated as $$\tau_h=Ke \quad (5),$$

the Formula (4) can be rewritten as $$\tau_m=Ke \quad (6).$$

Next, a procedure of performing the default calibration in the motionless state is described.

The default calibration in a motionless state is performed with the following steps.

(Step 1) A surface myoelectric potential e is measured when the wearer 12 is generating muscular strength countering the driving force (torque $\tau_m$) of the driving motors 20, 22, 24, 26.

(Step 2) A parameter K is obtained for satisfying the Formula (6) by using a least-squares method based on the measured surface myoelectric potential e and the corresponding input torque $\tau_m$.

The formula using the least-squares method for obtaining the parameter K is shown with the below-given Formula (7).

$$K=\Sigma\tau_m(t)e(t)/\tau e^2(t) \quad (7)$$

Accordingly, a parameter K can be obtained by satisfying a relationship where, for example, the value of the surface myoelectric potential becomes 1 when the wearer 12 having his/her knee joint bent approximately 90 degrees in a motionless sitting state generates a power of 1 Nm, as shown in FIG. 12. In this motionless state, the driving motors 20, 22, 24, 26 apply a driving force (torque $\tau_m$) as a load (input torque) to the wearer 12 step by step while the wearer 12 generates a muscular strength counterbalancing the driving force for maintaining the motionless state.

Next, a procedure of performing the reconfiguration calibration of predetermined basic movements is described.

The reconfiguration calibration for a single motion is performed with the following steps.

(Step 1) The wearer 12 rotates the knee joint so that the angle of the knee is changed from 90 degrees to 180 degrees and then the knee joint is returned to its original position so that the angle of the knee is changed from 180 degrees to 90 degrees.

(Step 2) The driving motor 20, 22, 24, 26 applies a driving force (torque $\tau_m$) according to the angle of the knee joint detected by the angle sensor 74, 76.

(Step 3) The surface myoelectric potential e generated upon extension and retraction of the knee by the wearer 12 is measured.

(Step 4) The parameter K satisfying the Formula (6) is obtained by using the least-squares method based on the measured surface myoelectric potential and the corresponding input torque $\tau_m$.

Next, the principle of executing the above-described default calibration is described with reference to FIGS. 13-15.

For example, a parameter K is obtained by applying a torque of 8 Nm, 16 Nm, 24 Nm, and 32 Nm to the wearer 12 from the driving motors 20, 22, 24, 26. FIGS. 13 and 14 show the results of calculating the virtual torque from the surface myoelectric potential generated from the calibration using the obtained parameter K and comparing the virtual torque with the corresponding input torque. It is to be noted that FIG. 13 is a graph showing the input torque (a) and the virtual torque (b) with respect to the extensor of the right hip joint. FIG. 14 is a graph showing the input torque (a) and the virtual torque (b) with respect to the flexor of the right hip joint.

Figure 13:
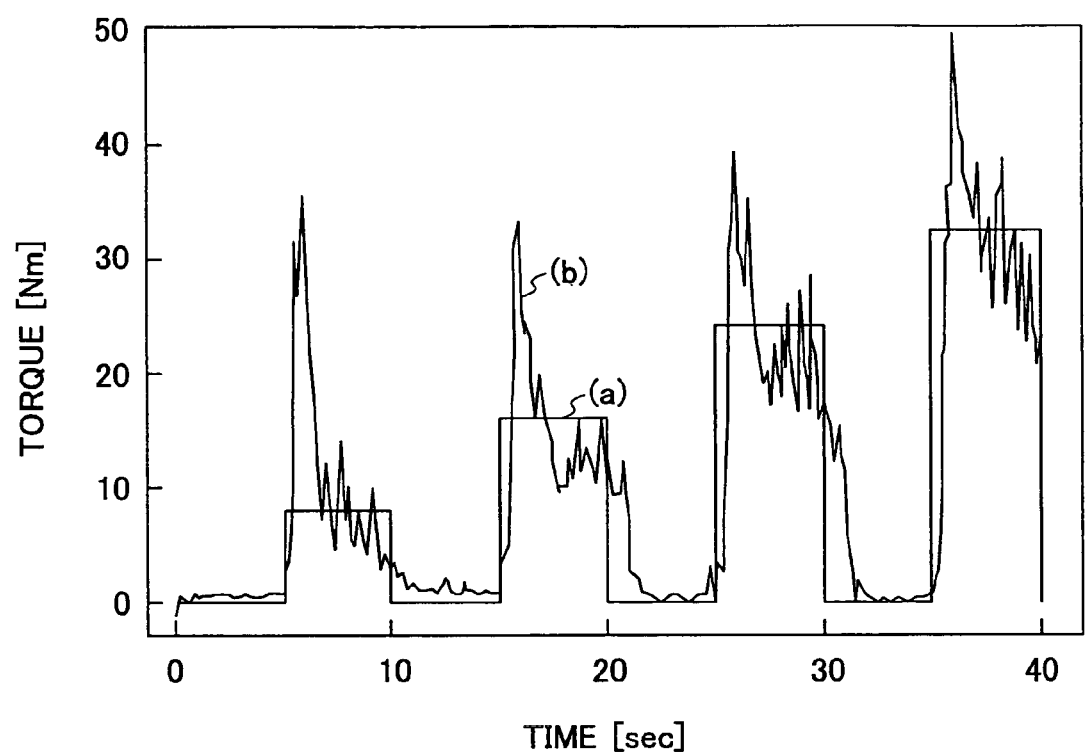
FIG. 13 is a graph showing an input torque and a virtual torque with respect to an extensor of a right hip joint.
Figure 14:
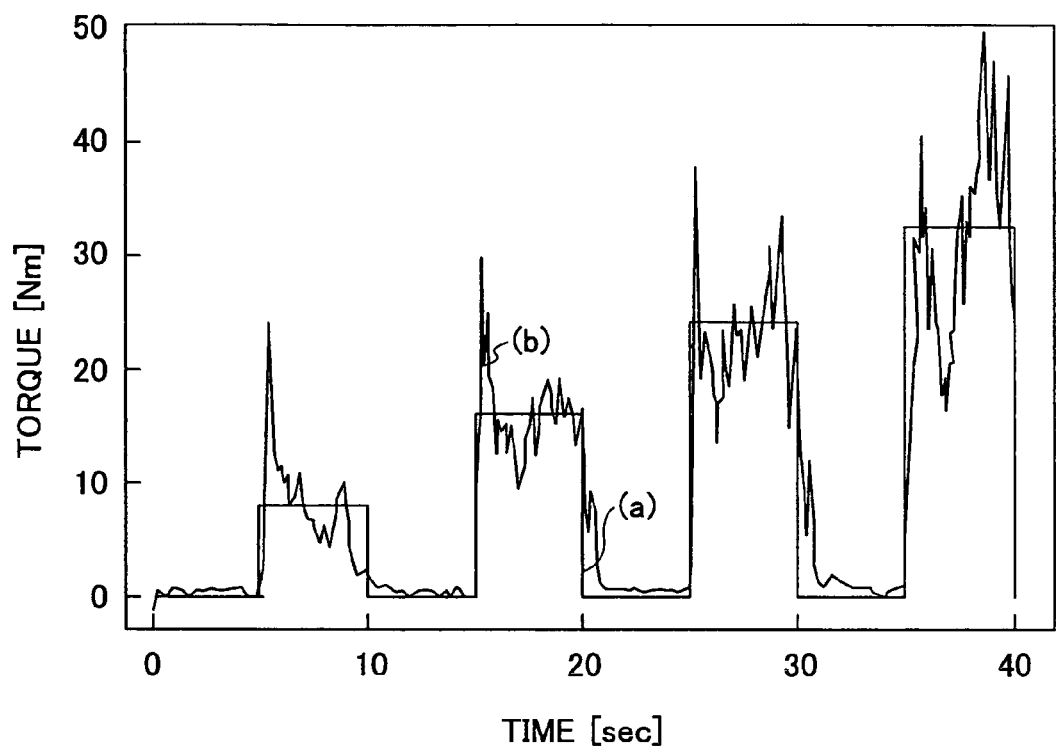
FIG. 14 is a graph showing an input torque and a virtual torque with respect to an flexor of a right hip joint.

By referring to the input torque of graph (a) and the virtual torque of graph (b) shown in FIG. 13 and the input torque of graph (a) and the virtual torque of graph (b) shown in FIG. 14, it can be understood that there is a relative match between the virtual torque calculated by using the parameter K using the above-described method and the input torque applied in correspondence to the movement.

Furthermore, as shown in graph (a) of FIG. 13, for the input torque from the driving motors 20, 22, 24, 26, the driving motors are controlled to have their torque value increased step by step along with the elapsing of time. That is, therefore, the driving motors 20, 22, 24, 26 are initially driven with a small torque value. Furthermore, the input torque is applied in a pulsed manner at predetermined intervals of time. Moreover, the value of the torque is controlled to increase step by step.

Accordingly, an excessive torque can be prevented from being applied when the wearer 12 wears the movement assisting wearing device 18. By increasing the value of input torque step by step, this reduces the load in generating muscular strength for countering the input torque. Thereby, the burden on the muscles during calibration can be reduced.

Furthermore, as shown in FIGS. 13 and 14, the same results can be attained for the left and right hip joints and the left and right knee joints. Furthermore, in a case of generating assisting force from the virtual torque by using the parameter K as described above, the driving motors 20, 22, 24, 26 can apply a driving force of 1 Nm as an assisting force with respect to the muscular strength 1 Nm generated by the wearer 12. Thereby, the wearer 12 can move by using half the muscular strength required for performing a predetermined movement.

Furthermore, in this embodiment, since it is necessary to generate muscular strength for countering input torque in a case where the wearer 12 wearing the movement assisting wearing device 18 performs calibration, calibration is performed by controlling the driving force of the driving motors 20, 22, 24, 26 so as to prevent too much load being applied to the wearer 12.

That is, in this embodiment, by having the wearer 12 perform a predetermined movement (for example, see FIG. 9 or FIG. 12) for performing calibration of the surface myoelectric potential, the calibration of the surface myoelectric potential can be performed without applying a large load on the wearer 12.

For example, in a case where a predetermined movement is performed twice, the virtual torque is to be the equal to the muscular strength generated from each joint in correspondence with the movement. Therefore, by storing virtual torque patterns corresponding to reference movements as reference data in the memory 130 beforehand, the parameter correction process during calibration can be conducted efficiently.

Thus, the following Formula (8) can be satisfied in a case where "$\tau_i(t)$" is the virtual torque obtained when the wearer 12 performs a predetermined movement by using parameter K obtained by the calibration of the wearer 12 and "$e'(t)$" is the surface myoelectric potential when the movement is performed again.

$$\tau_i(t) = Ke'(t) \tag{8}$$

Figure 15:
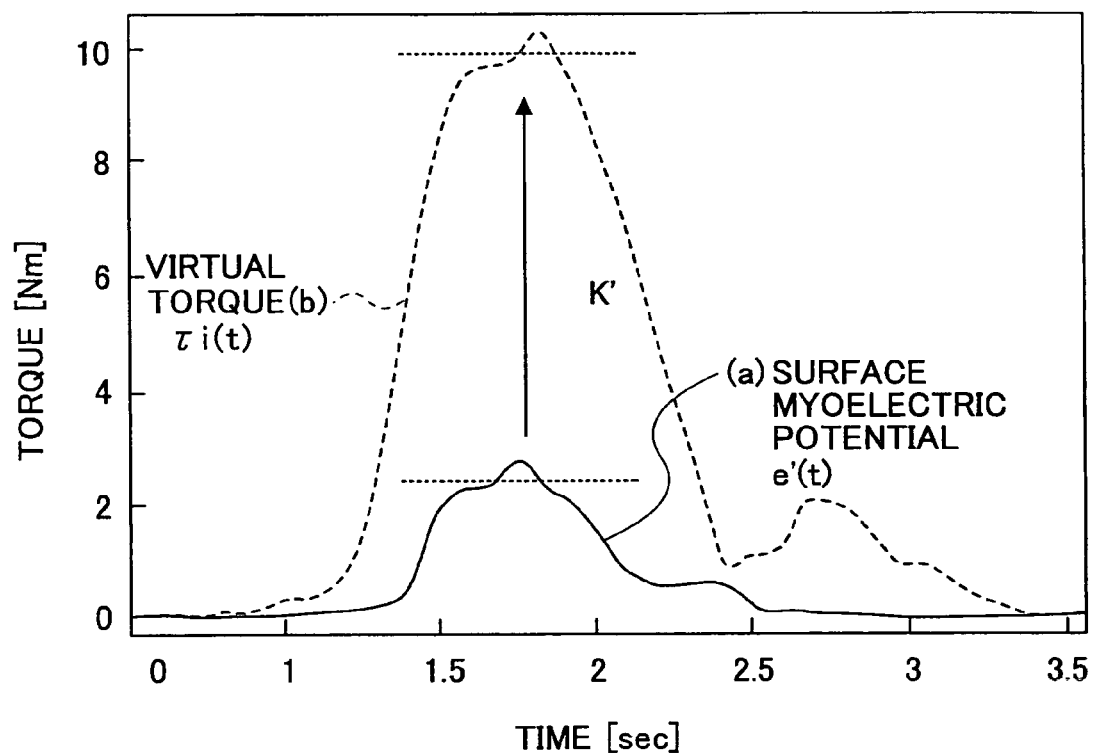
FIG. 15 is a graph showing a difference between surface myoelectric potential and virtual torque in a case where a wearer 12 performs the same movement as a predetermined reference movement.

With reference to FIG. 15, in a case of performing calibration of surface myoelectric potential, the surface myoelectric potential generated during a case where the wearer 12 performs the same movement as the reference predetermined movement (illustrated as a solid line in graph (a) of FIG. 15) is measured, and then the parameter K' is determined in a manner so that the virtual torque (illustrated as a broken line in graph (b) of FIG. 15) becomes equal to the input torque.

The following Formula (9) employed for calculating the parameter K' using a least-squares method is the same as the above-described Formula (7).

$$K' = \Sigma \tau_m(t) e'(t) / \Sigma e'^2(t) \tag{9}$$

Since the virtual torque $\tau_i$ is obtained by calibration using the wearable type movement assisting apparatus 10, it can be said that the obtained parameter K' is equal to that obtained by calibration using the wearable type movement assisting apparatus 10. Accordingly, an assisting force of 1 Nm can be applied to the wearer 12 in response to muscular strength of 1 Nm generated by the calibration method corresponding to the predetermined movement of the wearer 12.

Figure 16:
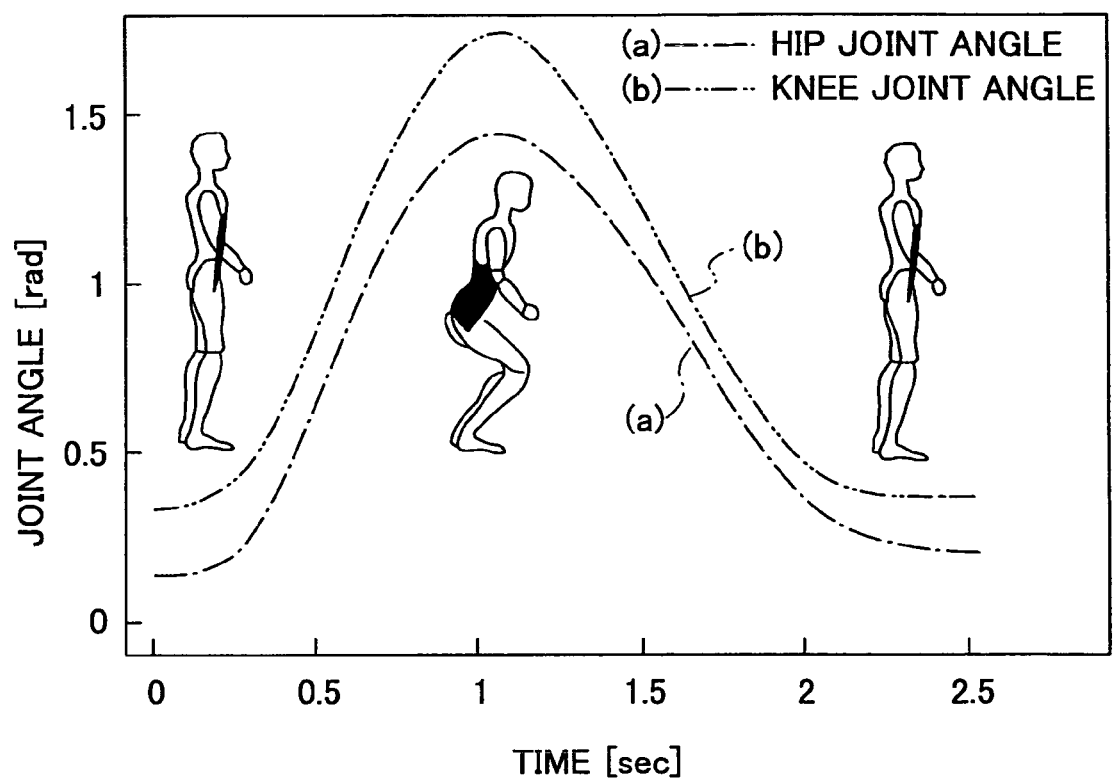
FIG. 16 is a graph showing changes of joint angle of a hip joint and changes of joint angle of a knee joint in correspondence with a bending and extending movement.
Figure 17:
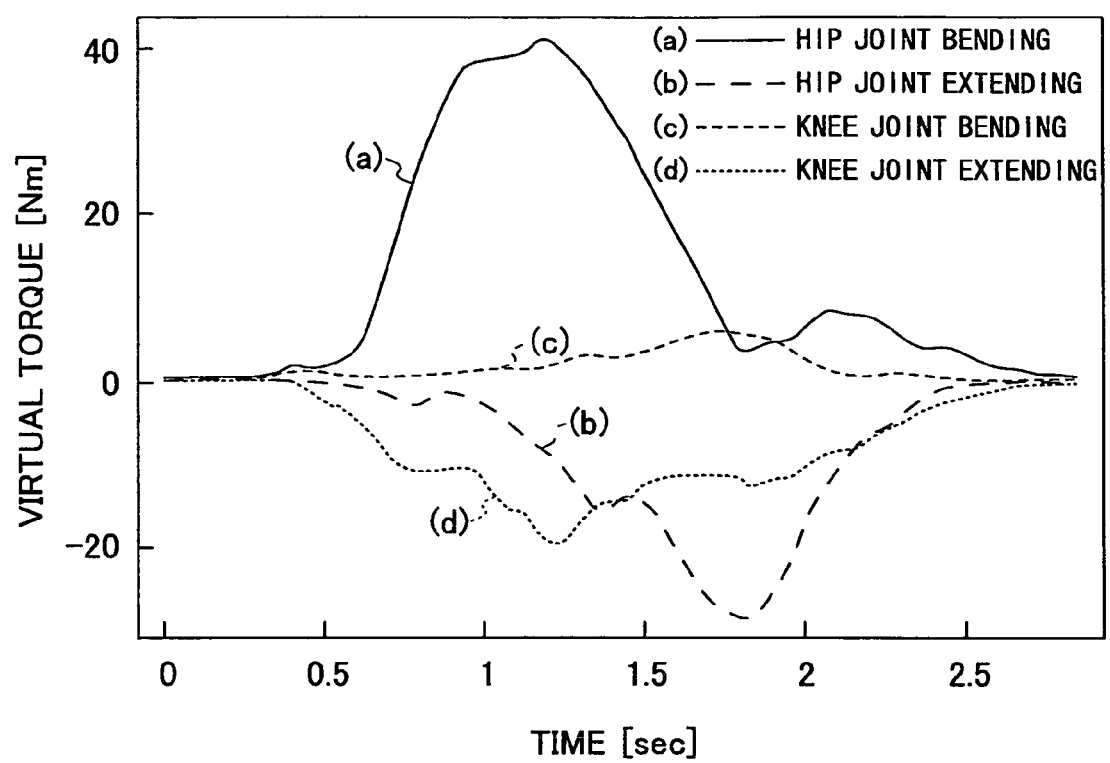
FIG. 17 is a graph showing a virtual torque of a bending movement of a hip joint, a virtual torque of an extending movement of a hip joint, a virtual torque of a bending movement of a knee joint, and a virtual torque of an extending movement of a knee joint in correspondence with a bending and extending movement.
Figure 18:
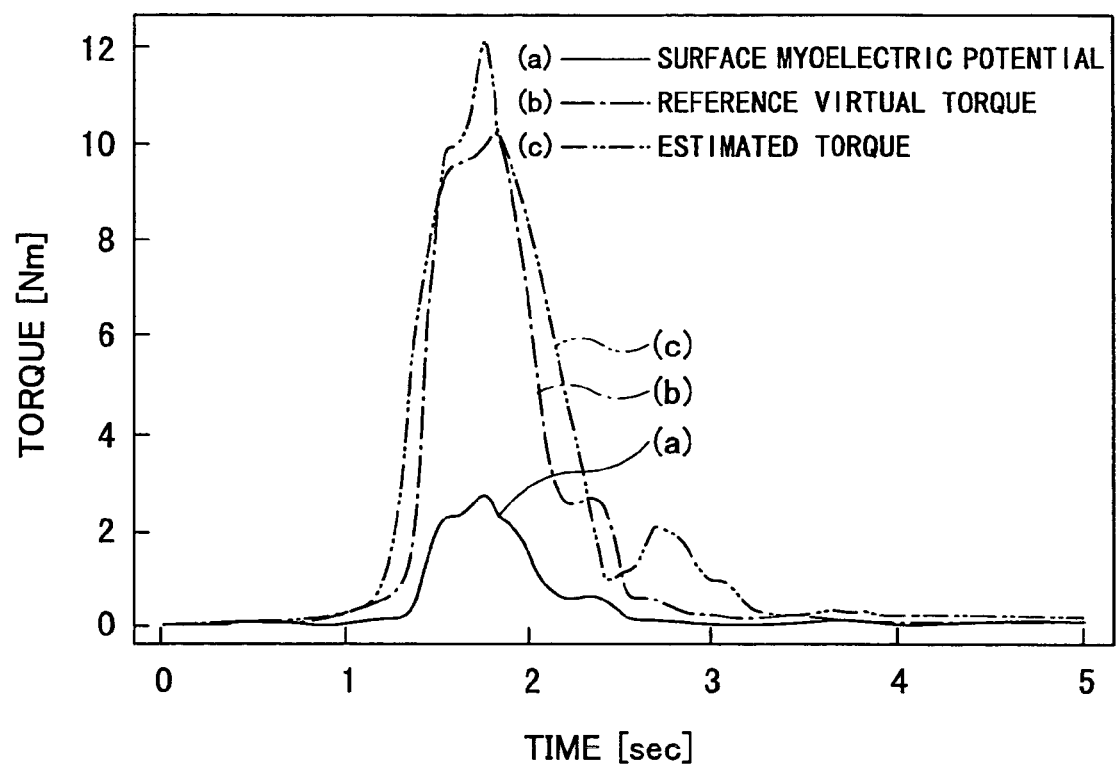
FIG. 18 is a graph showing a surface myoelectric potential of a bending movement of a hip joint, a reference virtual torque of a bending movement of a hip joint, and an estimated torque of an extending movement of a hip joint in correspondence with a bending and extending movement.

Next, FIGS. 17 and 18 show experiment results in a case where, for example, a bending and extending movement (as shown in FIG. 16) is the basic movement using a calibration according to an embodiment of the present invention.

Graph (a) of FIG. 17 shows joint angles of a hip joint that change in correspondence with a bending and extending movement, and graph (b) of FIG. 17 shows joint angles of a knee joint that change in correspondence with a bending and stretching movement.

In FIG. 18, graph (a) shows a virtual torque of a bending movement of a hip joint in association with a bending and extending movement, graph (b) shows a virtual torque of a extending movement of a hip joint in association with a bending and extending movement, graph (c) shows a virtual torque of a bending movement of a knee joint in association with a bending and extending movement, and graph (d) shows a virtual torque of a stretching movement of a knee joint in association with a bending and extending movement.

Figure 19:
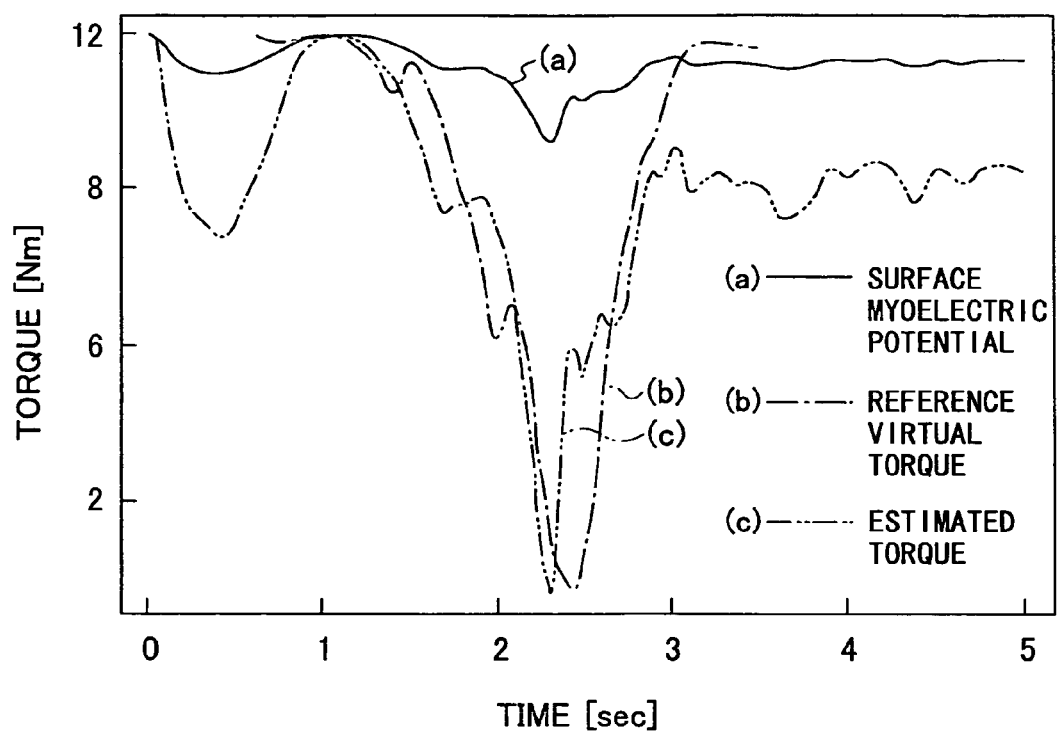
FIG. 19 is a graph showing a surface myoelectric potential of a extending movement of a hip joint, a reference virtual torque of a extending movement of a hip joint, and an estimated torque of a bending movement of a hip joint in correspondence with a bending and extending movement.

Next, in a case where the above-described bending and extending movement is performed as the basic movement, correction results of the flexor and the extensor of the right hip joint shown in FIGS. 18 and 19 are obtained when performing calibration according to the bending and extending movement. In FIG. 18, graph (a) shows the surface myoelectric potential of an extending movement of a hip joint in association with a bending movement, graph (b) shows a reference virtual torque of an extending movement of a hip joint in association with a bending movement, and graph (c) shows an estimated torque of an extending movement of a hip joint in association with a bending movement. Furthermore, in FIG. 19, graph (a) shows the surface myoelectric potential of a bending movement of a hip joint in association with a bending movement, graph (b) shows a reference virtual torque of a bending movement of a hip joint in association with a bending movement, and graph (c) shows an estimated torque of a bending movement of a hip joint in association with a bending movement.

According to graphs (a)-(c) shown in FIGS. 18 and 19, it can be understood that the virtual torque used as reference and the estimated torque of parameter K' obtained from calibration have similar amplitude waveforms and that the estimated torque in association with the bending and extending movement has substantially the same size as that of the virtual torque obtained from surface myoelectric potential.

Accordingly, in this embodiment, the wearer 12 can perform calibration of surface myoelectric potential by performing a predetermined movement. Thereby, the wearer 12 can be prevented from being applied with excessive load, and the parameter K' for obtaining a virtual torque (that is, calibrated surface myoelectric potential) can be calculated instantaneously.

It is to be noted that the torque applied as load to the wearer 12 can be set in accordance with the physical strength of each individual. For example, by setting the value of the upper limit of load and the value of the lower limit of load beforehand, the load during calibration can be adjusted so as to prevent excessive load to be applied to the wearer 12.

Next, a procedure of a main control process executed by the controlling apparatus 100 is described with reference to the flowchart shown in FIG. 20.

Figure 20:
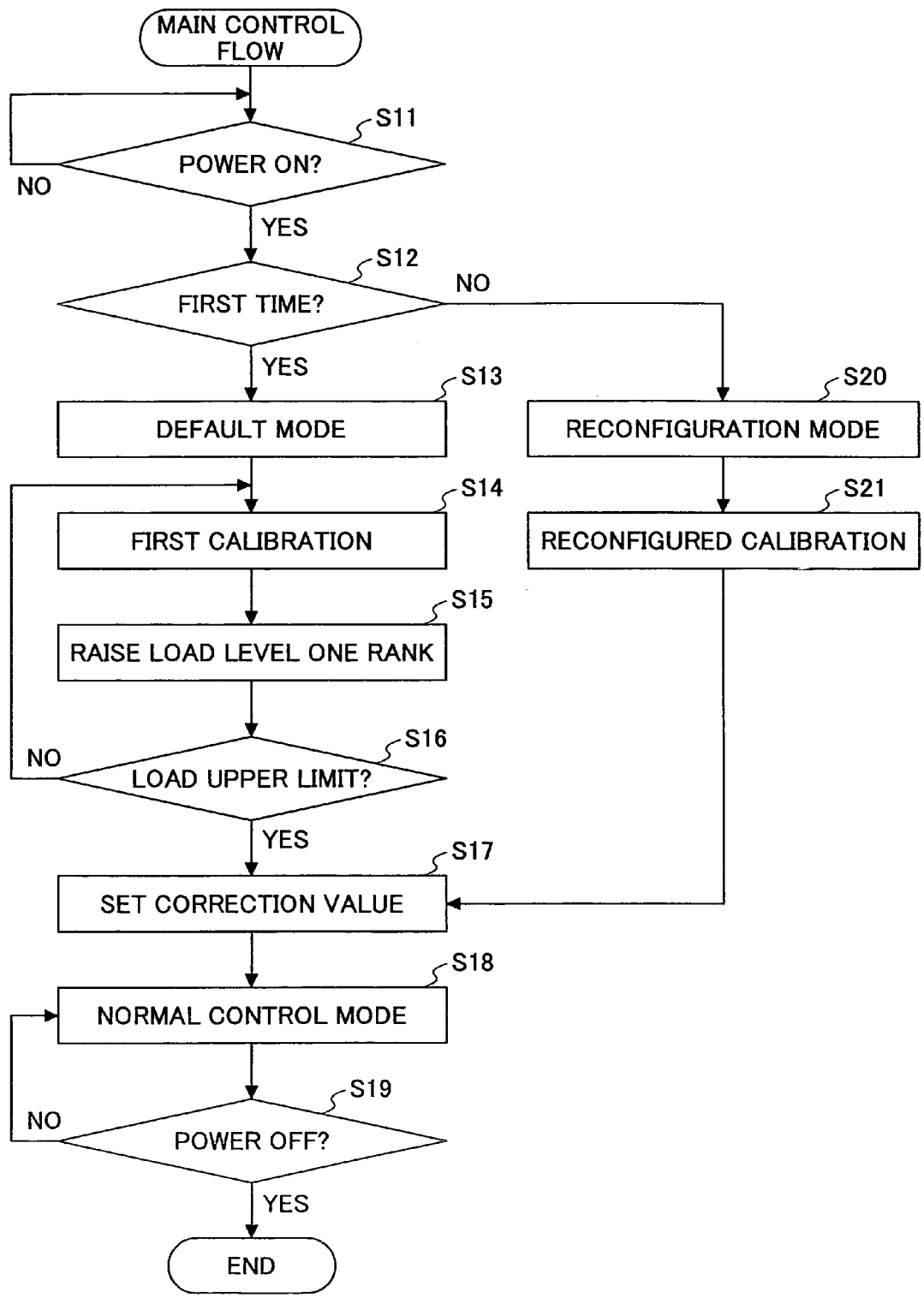
FIG. 20 is a flowchart for describing a procedure of a main control process executed by a controlling apparatus 100.

As shown in FIG. 20, when the movement assisting wearing device 18 is worn by the wearer 12 and its electric power switch (not shown) is turned on in Step S11 (hereinafter "Step" is omitted), the controlling apparatus 100 determines whether the operation of turning on the electric power switch is the first time in S12. In a case where it is the first time in S12, the controlling apparatus 100 transitions to a default mode in S13, and conducts a calibration process of the above-described default mode (corresponding to calibration part in claim 1) in S14.

That is, in S14, biosignals corresponding to driving force applied as load by the driving motors 20, 22, 24, 26 are detected from the detection signals of the surface myoelectric potential output from each myoelectric potential sensor 38a, 38b, 40a, 40b, 42a, 42b, 44a, 44b, and correction values are obtained based on the detection signals. In S15, the load is increased by increasing the voltage applied to the motors one rank. Next, in S16, it is determined whether the load has reached a predetermined upper limit value. In a case where the load has not reached the upper limit value in S16, the procedure returns to the above-described S14 to repeat the processes of S14-S16.

Furthermore, in a case where the load has reached the upper limit value in S16, a parameter K' obtained by the above-described calibration is set in S17.

In the subsequent S17, a correction value corresponding to the muscular strength of the wearer 12 obtained from the calibration in a motionless state (as in FIG. 12 showing the wearer 12 wearing the movement assisting wearing device 18). That is, in S15, a parameter K is obtained so that the value of the surface myoelectric potential becomes 1 in a case where the wearer 12 generates a force of 1 Nm when in a motionless sitting state with his/her knee joints bent approximately 90 degrees. In this calibration of the first time, the wearer 12 generates a muscular strength countering the driving force (torque $\tau_m$') applied as load (input torque) by the driving motors 20, 22, 24, 26.

Accordingly, by having each myoelectric potential sensor detect biosignals generated with respect to driving force applied by the driving source and generating a parameter for a calculation process based on the detected signals, the parameter is set to the database 148 as an inherent correction value of the wearer.

Thereby, based on the corresponding relationship between biosignals and the power generated by a process of a predetermined basic movement of the wearer 12 (second corresponding relationship), assisting power can be corrected in correspondence with the biosignals whenever the movement assisting wearing device 18 is worn by the wearer 12 in a manner that the corresponding relationship between the biosignals and the power generated by the wearer 12 (first corresponding relationship) is satisfied.

Then, it transitions to a normal control mode for conducting an assisting force control process in S18. Then, the normal control mode is continued until the electric power switch is turned off in Step 19.

Furthermore, in a case where the operation of turning on the electric power switch is the second time or more in S12, it transitions to the above-described reconfiguration mode in S20. Then, in S21, a correction value setting calibration (corresponding to calibration part in claim 1) for one motion (single movement) of the wearer 12 is conducted, and a correction value (parameter K') is set in correspondence with the muscular strength of the wearer 12 obtained from the calibration movement (as shown in FIG. 16). Then, the processes of the above-described S17-S19 are conducted.

It is however to be noted that this embodiment is not limited to conducting calibration for one motion after the second time or more. The correction value setting calibration may be performed after the second time or more in the same manner as the motionless state of the first time.

Next, a control process for each correction value setting mode is described with reference to FIGS. 21-23.

Figure 21:
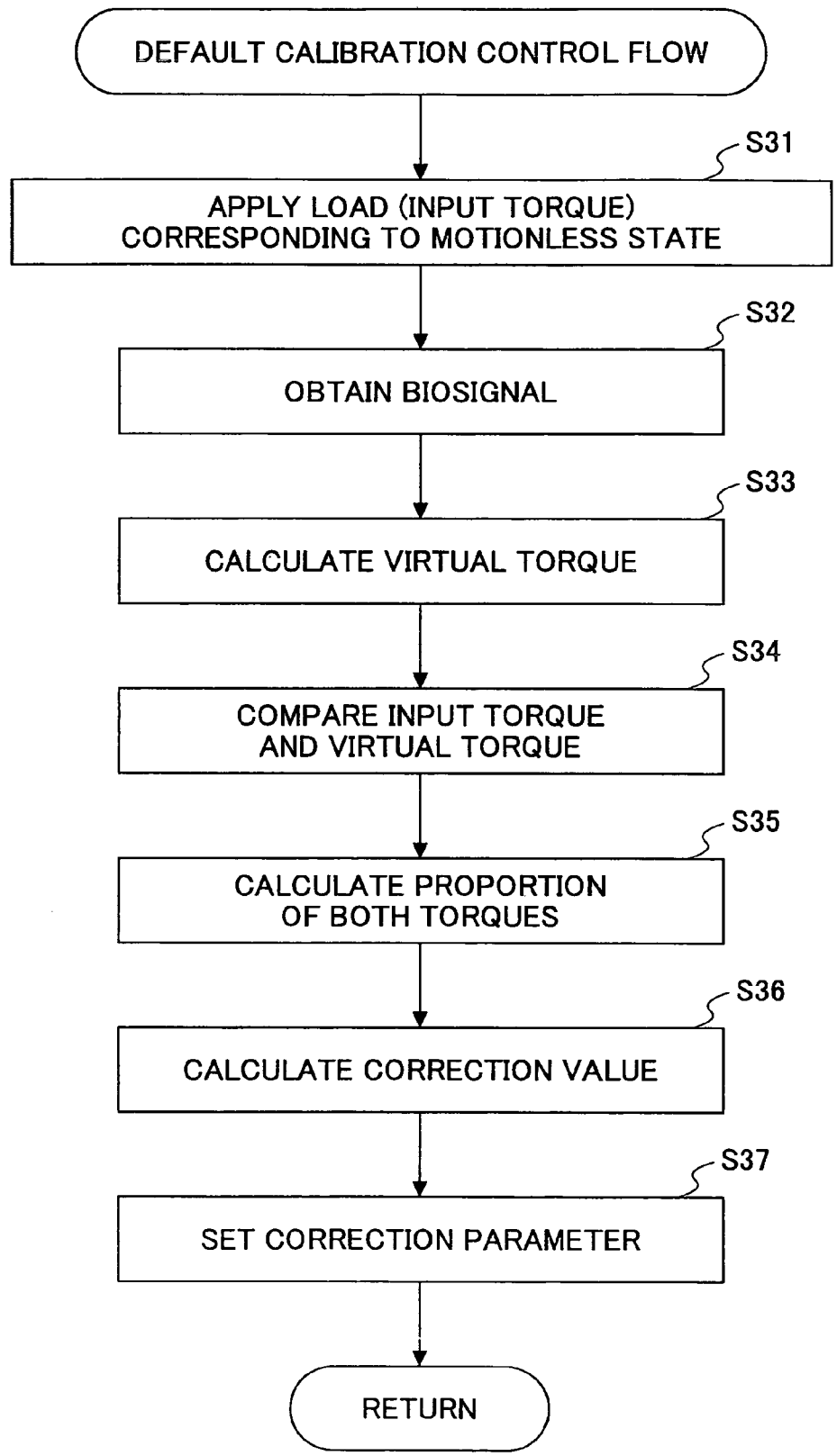
FIG. 21 is a flowchart for describing a control procedure of a first calibration performed for setting a default in a motionless state.

FIG. 21 is a flowchart showing a control procedure of a calibration of a first time that is executed as a default. It is to be noted that, in a case of calibration for the first time, the above-described correction value is set by having the wearer 12 generate a muscular strength for maintaining a motionless sitting state with respect to the load from the motor.

As shown in FIG. 21, the controlling apparatus 100 provides a driving force (input torque) as a load by supplying a predetermined driving current to the driving motors 20, 22, 24, 26 in correspondence with the sitting motionless state of the wearer 12. Accordingly, the wearer 12 generates a muscular strength in the sitting state for countering the driving force of the driving motors 20, 22, 24, 26.

Then, in S32, myoelectric potential signals of the wearer 12 are obtained from each myoelectric potential sensor 38a, 38b, 40a, 40b, 42a, 42b, 44a, 44b. Then, in S33, based on the measured myoelectric potential signals, a virtual torque is estimated by calculation.

Then, in S34, the input torque applied as load is compared with the above-described virtual torque. Then, in S35, the proportion between the input torque and the virtual torque is calculated. Then, in S36, a parameter corresponding to each phase stored in the above-described calibration database 148 is read out for multiplying the above-described proportion with this parameter, to thereby obtain a correction value (correction parameter) of the control signals supplied to the motor drivers 92-95. Then, in S37, the correction parameter is set as the parameter for autonomous control (corresponding to correction value setting part in claim 2).

Accordingly, the wearer 12 wearing the movement assisting wearing device 18 can automatically perform calibration of biosignals in a sitting state without requiring any laborious procedures for performing calibration such as attaching weights as a load to the wearer or attaching a coil spring as an alternative to the weights are required. Accordingly, the time and effort required for calibration can be reduced significantly. This will further promote putting the wearable type movement assisting apparatus 10 into practical use and popularizing the wearable type movement assisting apparatus 10.

Furthermore, the correction value can be set in correspondence with the state of the wearer 12 having weakened muscular strength without applying excessive load on the wearer 12 for performing calibration. This enables the correction value to be set according to the state of the wearer 12 and a driving force to be accurately applied to the wearer 12 in cooperation with the movement of the wearer 12 based on the myoelectric potential of the wearer 12.

Therefore, an assisting force from the driving source can be applied in accordance with the will of the wearer 12 during the execution of calibration. Accordingly, the movement of the wearer 12 can be stably assisted without applying too much or too little assisting force. Thereby, reliability of the wearable type movement can be further improved.

Particularly, the wearer 12 can perform calibration with ease even in a case where manipulation of a worn movement assisting wearing device 18 is considered to be difficult, such as a case where the wearer 12 is a beginner. Therefore, even in a case where the wearer 12 has difficulty in moving freely (such as a physically impaired person), calibration can be performed while avoiding movement difficult for the wearer 12, and calibration can be performed in a manner complementing the physical deficiencies of the wearer.

Next, the above-described calibration of the reconfiguration mode 1 is described with reference to FIG. 22.

FIG. 22 is a flowchart showing a control procedure of a reconfiguration calibration for one motion (single movement). It is to be noted that the wearer 12 moves his/her knees from a bent state to an extended state one time while in a sitting position in the case of performing calibration for one motion. Furthermore, reference myoelectric potentials corresponding to calibration movements are stored in the memory 130.

As shown in FIG. 22, the controlling apparatus 100 determines whether there are any detection signals from the angle sensors 74, 76 of the knee joints in S41. In a case where the angle sensors 74, 76 detect changes of joint angle of the second joint 66 along with the knee extending movement of the wearer 12 in a sitting state (as shown in FIG. 16), a movement angle of the knee is set based on the detection signals from the angle sensor 74, 76 in S42.

Then, in S43, a reference myoelectric potential corresponding to the movement angle of the knee is readout from the memory 130. Then, in S44, the measured values of myoelectric potential of the wearer 12 are read out from each myoelectric potential sensor 38a, 38b, 40a, 40b, 42a, 42b, 44a, 44b. Then, in S45, the reference myoelectric potential and the measured value of the myoelectric potential are compared.

Then, in S46, the proportion between the reference myoelectric potential and the measured value of the myoelectric potential is calculated. Then, in S47, a correction value (correction parameter) of the control signal provided to the motor drivers 92-95 is calculated by reading out a parameter corresponding to the movement angle of the knee from the calibration database 148 and multiplying the parameter with the above-described proportion. Then, in S48, the correction parameter is set as the parameter for autonomous control (corresponding to correction value setting part in claim 2).

Accordingly, in the calibration for the second time or more, the parameter K' can be corrected by moving the knee in a sitting state (one motion) without using the driving force of the driving motors 20, 22, 24, 26. Thereby, the physical load of the wearer 12 can be reduced considerably and the time required in preparing calibration after wearing the movement assisting wearing device 18 can be shortened. Accordingly, the calibration for the second time or more allows walking to be started early.

Next, the above-described calibration of the reconfiguration mode 2 is described with reference to FIG. 23. In the reconfiguration mode 2, the wearer 12 performs a reference movement of standing up from a sitting state (phase A1-A4) and then returning to a sitting state (phase A4-A1) (See FIG. 9).

As shown in FIG. 23, the controlling apparatus 100 determines whether there are any detection signals from the angle sensors 70, 72, 74, 76 of the movement assisting wearing device 18 in S51. In a case where the angle sensors 70, 72, 74, 76 detect changes of joint angle of the first and second joints 64, 66 along with the movement shown in FIG. 9, a reference movement of the wearer 12 is set in S52 by selecting a task stored in the calibration database 148 according to the detection signals from the angle sensors 70, 72, 74, 76.

Then, reference myoelectric potentials corresponding to the reference movements of the first and second joints 64, 66 are read out from the memory 130. Then, the measured values of myoelectric potential of the wearer 12 are read out from each myoelectric potential sensor 38a, 38b, 40a, 42a, 42b, 44a, 44b in S54. Then, the reference myoelectric potential and the measured myoelectric potential are compared in S55.

Then, the proportion between the reference myoelectric potential and the measured value of the myoelectric potential is calculated in S56. Then, in S57, a correction value (correction parameter) of the control signal provided to the motor drivers 92-95 is calculated by reading out a parameter corresponding to the movement angle of the knee from the calibration database 148 and multiplying the parameter with the above-described proportion. Then, in S58, the correction parameter is set as the parameter for autonomous control (corresponding to correction value setting part in claim 2).

Then, in S59, it is determined whether the task of the calibration movement is finished. In a case where there is a remaining phase in S59, the next phase is updated in S60, the processes of the above-described S53 and those after are performed again.

Furthermore, in a case where the task of the calibration movement is finished, the calibration operation is finished.

Accordingly, in the calibration for the second time or more, the parameter K' can be corrected without using the driving force of the driving motors 20, 22, 24, 26. Thereby, the physical load of the wearer 12 can be reduced considerably and the time required in preparing calibration after wearing the movement assisting wearing device 18 can be shortened.

Therefore, calibration suited for the individual can be performed such as performing calibration of surface myoelectric potential according to a bending and extending movement of the wearer 12 or performing calibration according to a reference movement where the wearer 12 bends and extends his/her knees in a sitting state. Accordingly, even in a case where the wearer 12 is a physically impaired person, calibration can be performed according to a given movement that can be performed by the physically impaired person or according to a reference movement of other movements (tasks).

INDUSTRIAL APPLICABILITY

It is to be noted that the above-described embodiment is not limited to the above-described example of a movement assisting apparatus configured to provide an assisting force to the legs of the wearer 12. For example, the present invention may be applied to a movement assisting apparatus configured to assist the movement of arms.

Furthermore, although the above-described embodiment describes a configuration of transmitting a driving torque of an electric motor as assisting force, the present invention may be applied to an apparatus generating an assisting force by a driving source other than an electric motor.

The invention claimed is:
1. A wearable type movement-assisting apparatus comprising:
   a detecting part for detecting a biosignal from a wearer, the biosignal being a potential generated by the wearer,
   a movement assisting wearing device including a driving source for applying a driving force to the wearer,
   a control part for controlling the driving source to generate an assisting force based on a parameter, so that the assisting force is applied to the wearer in correspondence with the biosignal detected by the detecting part,
   a parameter correcting part for estimating a virtual torque of the wearer according to the biosignal and correcting the parameter based on a relationship between the biosignal and the virtual torque as a unique parameter of the wearer,
   a calibration part for performing a default calibration to initially set the parameter and a reconfiguration calibration to update the parameter corrected by the parameter correcting part according to the biosignal that is generated in response to the driving force applied from the driving source,
   wherein the calibration part is configured to perform the default calibration when the wearable type movement assisting apparatus is worn for the first time by the wearer,
   wherein the calibration part is configured to perform the reconfiguration calibration each time the wearable type movement assisting apparatus is worn after the default calibration,
   wherein the default calibration includes a motionless state calibration in which the wearer generates muscular strength in a motionless state, and
   wherein the reconfiguration calibration is executed as a one motion calibration in which the wearer moves a joint from a bent state to an extending state.
2. The wearable type movement-assisting apparatus as claimed in claim 1, further comprising:

a load generating part for generating the driving force to be applied by the driving source as an external force when the movement assisting wearing device is worn by the wearer.

3. The wearable type movement-assisting apparatus as claimed in claim 1, wherein the calibration part includes a database storing a corresponding relationship between the biosignal detected by the detecting part and a control signal for controlling the driving source,
wherein the control part corrects the control signal stored in the database according to a correction value set by the parameter correcting part.

4. The wearable type movement-assisting apparatus as claimed in claim 1, wherein the detecting part is adapted to be adhered on the wearer's skin and detects a myoelectric potential of the wearer as the biosignal.

5. The wearable type movement-assisting apparatus as claimed in claim 1, wherein the movement assisting wearing device includes
a waist belt,
a right leg assisting part provided at a right side below the waist belt, and
a left let assisting part provided at a left side below the waist belt,
wherein the right leg assisting part and the left leg assisting part includes
a first frame extending downward in a manner supporting the waist belt,
a second frame extending downward from the first frame,
a third frame extending downward from the second frame,
a fourth frame on which a bottom side of a foot of the wearer is adapted to be placed and provided at a lower end of the third frame,
a first joint interposed between a lower end of the first frame and an upper end of the second frame, and
a second joint interposed between a lower end of the second frame and an upper end of the third frame.

6. The wearable type movement-assisting apparatus as claimed in claim 5, wherein the first joint is adapted to be provided at a level matching the height of the hip joint of the wearer,
wherein the second joint is adapted to be provided at a level matching the height of the knee joint of the wearer.

7. The wearable type movement-assisting apparatus as claimed in claim 5, wherein a first driving source is provided in the first joint for transmitting a driving force for rotating the second frame, and
wherein a second driving source is provided in the second joint for transmitting a driving force for rotating the third frame.

8. The wearable type movement-assisting apparatus as claimed in claim 7, wherein the first and second driving sources include an angle sensor for detecting a joint angle.

9. A calibration apparatus of a wearable type movement-assisting apparatus for performing a calibration whenever a wearer wears a movement-assisting wearing device including a driving source generating an assisting power corresponding to biosignals from the wearer by associating the biosignals and the assisting power to a predetermined relationship, the biosignals being potentials generated by the wearer, the assisting power generated by the driving source being controlled based on a parameter, the calibration apparatus comprising:
a first storage part for storing a first corresponding relationship between a first power generated by the wearer and a first biosignal generated by the wearer in response to a driving force applied by the driving source when the wearer wears the movement-assisting wearing device; and
a second storage part for storing a second corresponding relationship between a second power generated by the wearer and a second biosignal generated by the wearer during a process of performing a predetermined basic movement;
wherein based on the second biosignal generated during the basic movement of the wearer and the second corresponding relationship, a correction of the parameter is performed for satisfying the first corresponding relationship whenever the movement-assisting wearing device is worn by the wearer,
wherein the calibration includes a default calibration to initially set the parameter and a reconfiguration calibration to correct and update the parameter set by the default calibration,
wherein the default calibration is performed when the wearable type movement assisting apparatus is worn for the first time by the wearer,
wherein the reconfiguration calibration is performed each time the wearable type movement assisting apparatus is worn after the default calibration,
wherein the default calibration includes a motionless state calibration in which the wearer generates muscular strength in a motionless state, and
wherein the reconfiguration calibration is executed as a one motion calibration in which the wearer moves a joint from a bent state to an extending state.

10. The calibration apparatus of the wearable type movement-assisting apparatus as claimed in claim 9, wherein the first corresponding relationship includes the first power having a positive correlation with respect to the first biosignal, wherein the second corresponding relationship includes a relationship between changes of the respective first and second biosignals and changes of the first and second power of the basic movement.

11. A nontransitory computer readable storage device that stores a program which, when executed by a computer, causes the computer to execute a calibration method for performing a calibration whenever a wearer wears a movement-assisting wearing device including a driving source generating an assisting power corresponding to biosignals from the wearer by associating the biosignals and the assisting power to a predetermined relationship, the biosignals being potentials generated by the wearer, the assisting power generated by the driving source being controlled based on a parameter, the method comprising:
storing in a first storage part a first corresponding relationship between a first power generated by the wearer and a first biosignal generated by the wearer in response to a driving force applied by the driving source when the wearer wears the movement-assisting wearing device and storing in a second storage part a second corresponding relationship between a second power generated by the wearer and a second biosignal generated by the wearer during a process of performing a predetermined basic movement; and
performing correction of the parameter based on the second biosignal generated during the basic movement of the wearer and the second corresponding relationship stored in the second storage part when the movement-assisting wearing device is worn by the wearer for satisfying the first corresponding relationship stored in the first storage part, wherein the calibration includes a default calibration to initially set the parameter and a reconfiguration calibration to correct and update the parameter set by the default calibration, wherein the default calibration is performed when the movement-assisting wearing device is worn for the first time by the wearer, wherein the reconfiguration calibration is performed each time the movement-assisting wearing device is worn after the default calibration, wherein the default calibration includes a motionless state calibration in which the wearer generates muscular strength in a motionless state, and wherein the reconfiguration calibration is executed as a one motion calibration in which the wearer moves a joint from a bent state to an extending state.

\* \* \* \* \*